(12) United States Patent
Hanson et al.

(10) Patent No.: US 9,485,991 B2
(45) Date of Patent: Nov. 8, 2016

(54) MODULATION OF PLANT BIOLOGY

(71) Applicant: FBSCIENCES HOLDINGS, INC., Collierville, TN (US)

(72) Inventors: Terry J. Hanson, Raleigh, NC (US); Kenneth Scott Day, Clovis, CA (US); Johan Peter Stromberg, Germantown, TN (US)

(73) Assignee: FBSCIENCES HOLDINGS, INC., Collierville, TN (US)

( * ) Notice: Subject to any disclaimer, the term of this patent is extended or adjusted under 35 U.S.C. 154(b) by 0 days.

(21) Appl. No.: 13/739,669

(22) Filed: Jan. 11, 2013

(65) Prior Publication Data

US 2013/0184151 A1  Jul. 18, 2013

Related U.S. Application Data

(60) Provisional application No. 61/585,848, filed on Jan. 12, 2012.

(51) Int. Cl.
| | |
|---|---|
| *A01N 37/36* | (2006.01) |
| *A01N 57/00* | (2006.01) |
| *A01N 61/00* | (2006.01) |
| *A01N 25/28* | (2006.01) |
| *A01N 59/00* | (2006.01) |

(52) U.S. Cl.
CPC ............. *A01N 57/00* (2013.01); *A01N 25/28* (2013.01); *A01N 37/36* (2013.01); *A01N 59/00* (2013.01); *A01N 61/00* (2013.01)

(58) Field of Classification Search
None
See application file for complete search history.

(56) References Cited

U.S. PATENT DOCUMENTS

| | | | |
|---|---|---|---|
| 2,200,532 A | 12/1939 | Sherman | |
| 3,544,296 A | 12/1970 | Karcher | |
| 3,958,016 A | 5/1976 | Galle et al. | |
| 4,069,034 A | 1/1978 | Hoover | |
| 4,245,432 A | 1/1981 | Dannelly | |
| 4,249,343 A | 2/1981 | Dannelly | |
| 4,272,920 A | 6/1981 | Dawson | |
| 4,337,077 A | 6/1982 | Rutherford | |
| 4,367,609 A | 1/1983 | Lloyd | |
| 4,624,694 A | 11/1986 | Delli Colli | |
| 4,657,576 A * | 4/1987 | Lambie | 71/64.07 |
| 4,698,090 A | 10/1987 | Marihart | |
| 4,769,221 A | 9/1988 | Marihart | |
| 4,786,307 A | 11/1988 | Marihart | |
| 4,828,600 A | 5/1989 | McCabe et al. | |
| 4,875,921 A | 10/1989 | Paau | |
| 4,878,936 A | 11/1989 | Handelsman et al. | |
| 5,026,416 A | 6/1991 | Alexander | |
| 5,044,116 A | 9/1991 | Gago et al. | |
| 5,087,475 A | 2/1992 | Bazin et al. | |
| 5,129,180 A | 7/1992 | Stewart | |
| 5,178,661 A | 1/1993 | Van Der Watt et al. | |
| 5,183,477 A | 2/1993 | Masuda | |
| 5,204,368 A | 4/1993 | Cronje et al. | |
| 5,250,500 A | 10/1993 | Jones et al. | |
| 5,300,127 A | 4/1994 | Williams | |
| RE34,670 E | 7/1994 | Williams et al. | |
| 5,525,131 A | 6/1996 | Asano | |
| 5,593,947 A | 1/1997 | Kinnersley | |
| 5,599,769 A | 2/1997 | Hacker et al. | |
| 5,665,671 A | 9/1997 | Zanin | |
| 5,747,020 A | 5/1998 | Rutherford et al. | |
| 5,849,320 A | 12/1998 | Turnblad et al. | |
| 5,928,997 A | 7/1999 | Bauer et al. | |
| 5,939,089 A | 8/1999 | Wirtz et al. | |
| 5,939,356 A | 8/1999 | Wellinghoff | |
| 5,951,978 A | 9/1999 | Red'kina | |
| 6,022,744 A | 2/2000 | Tetteroo et al. | |
| 6,074,988 A | 6/2000 | King | |
| 6,077,505 A | 6/2000 | Parke et al. | |
| 6,080,220 A | 6/2000 | Sequi et al. | |
| 6,080,319 A | 6/2000 | Alther | |
| 6,083,293 A | 7/2000 | Bath et al. | |
| 6,083,877 A | 7/2000 | Kinnersley et al. | |
| 6,090,750 A | 7/2000 | Chollet et al. | |
| 6,121,193 A | 9/2000 | Segaud et al. | |
| 6,199,318 B1 | 3/2001 | Stewart et al. | |
| 6,261,996 B1 | 7/2001 | Klittich et al. | |
| 6,277,787 B1 | 8/2001 | Malefyt et al. | |
| 6,284,709 B1 | 9/2001 | Ju | |
| 6,372,008 B1 | 4/2002 | Boote et al. | |
| 6,434,884 B1 | 8/2002 | Hartung | |

(Continued)

FOREIGN PATENT DOCUMENTS

| | | |
|---|---|---|
| CA | 1328238 | 4/1994 |
| CA | 2056107 | 7/1998 |

(Continued)

OTHER PUBLICATIONS

Ajouri, Aziza, Haben Asgedom, and Mathias Becker. "Seed priming enhances germination and seedling growth of barley under conditions of P and Zn deficiency." Journal of Plant Nutrition and Soil Science 167.5 (2004): 630-636.*

(Continued)

*Primary Examiner* — Abigail Fisher
*Assistant Examiner* — Daniel Branson
(74) *Attorney, Agent, or Firm* — Christopher J. Knors; Moore & Van Allen PLLC

(57) ABSTRACT

A method of effecting at least one biological process in a plant is disclosed. The method comprises contacting a part of a seed, a plant, or the locus thereof with a mixture comprising an agriculturally acceptable mixture of (i) complex polymeric polyhydroxy acids and (ii) a phytotoxic amount of one or more alkali (earth) salts and/or a synergistic amount of at least one source of an agriculturally acceptable transition metal ions.

22 Claims, 22 Drawing Sheets

(56) References Cited

U.S. PATENT DOCUMENTS

| | | |
|---|---|---|
| 6,447,810 B1 | 9/2002 | Choi |
| 6,453,608 B1 | 9/2002 | Flanagan et al. |
| 6,458,747 B1 | 10/2002 | Kulik |
| 6,557,298 B2 | 5/2003 | Obert et al. |
| 6,645,267 B1 | 11/2003 | Dinel |
| 6,669,849 B1 | 12/2003 | Nguyen |
| 6,673,375 B2 | 1/2004 | Choi |
| 6,698,137 B2 | 3/2004 | Muhr |
| 6,855,536 B2 | 2/2005 | Loh et al. |
| 6,884,440 B2 | 4/2005 | Choi |
| 6,899,900 B2 | 5/2005 | Choi |
| 6,911,415 B1 | 6/2005 | Ueland et al. |
| 6,916,650 B2 | 7/2005 | Arndt |
| 7,001,869 B2 | 2/2006 | Johnson |
| 7,003,914 B2 | 2/2006 | Legro et al. |
| 7,182,951 B1 | 2/2007 | Balachander et al. |
| 7,213,367 B2 | 5/2007 | Wertz et al. |
| 7,291,272 B2 | 11/2007 | Bourke |
| 7,393,678 B2 | 7/2008 | Triplett et al. |
| 7,510,590 B2 | 3/2009 | Anaya-Olvera |
| 7,540,965 B2 | 6/2009 | Sengupta |
| 7,687,434 B2 | 3/2010 | De Billot et al. |
| 7,763,666 B2 | 7/2010 | Vero |
| 7,785,474 B2 | 8/2010 | Vero |
| 2002/0053229 A1 | 5/2002 | Varshovi |
| 2002/0095864 A1 | 7/2002 | Obert et al. |
| 2002/0098980 A1 | 7/2002 | Choi |
| 2002/0134012 A1 | 9/2002 | Ding et al. |
| 2003/0044382 A1 | 3/2003 | Selvig et al. |
| 2003/0051523 A1 | 3/2003 | Tabei |
| 2003/0130120 A1 | 7/2003 | Ziemer et al. |
| 2003/0185900 A1 | 10/2003 | Choi |
| 2003/0206967 A1 | 11/2003 | Choi |
| 2003/0228679 A1 | 12/2003 | Smith et al. |
| 2003/0228981 A1 | 12/2003 | Wertz et al. |
| 2004/0077498 A1 | 4/2004 | Lynch |
| 2004/0118040 A1 | 6/2004 | Asrar et al. |
| 2004/0261481 A1 | 12/2004 | Anaya-Olvera |
| 2005/0065034 A1 | 3/2005 | Miele |
| 2005/0197251 A1 | 9/2005 | Ding et al. |
| 2005/0197253 A1 | 9/2005 | Stoller et al. |
| 2005/0220834 A1 | 10/2005 | Wang |
| 2006/0032120 A1 | 2/2006 | McPherson |
| 2006/0032281 A1 | 2/2006 | Meyer |
| 2006/0229203 A1 | 10/2006 | Peltonen et al. |
| 2007/0039365 A1 | 2/2007 | King et al. |
| 2007/0068072 A1 | 3/2007 | Xavier et al. |
| 2007/0074451 A1 | 4/2007 | Pearce et al. |
| 2007/0095118 A1 | 5/2007 | Evers |
| 2007/0135506 A1 | 6/2007 | Zeun et al. |
| 2007/0212772 A1 | 9/2007 | Hill et al. |
| 2007/0249498 A1 | 10/2007 | Van Der Drift |
| 2008/0004178 A1 | 1/2008 | Ding et al. |
| 2008/0242544 A1 | 10/2008 | Duckham et al. |
| 2008/0274885 A1 | 11/2008 | Martin et al. |
| 2009/0105076 A1 | 4/2009 | Stewart et al. |
| 2009/0105077 A1 | 4/2009 | Bhatti |
| 2009/0199314 A1 | 8/2009 | Gaudillat |
| 2010/0010089 A1 | 1/2010 | Van Dyke |
| 2010/0016162 A1* | 1/2010 | Goodwin ............ 504/187 |
| 2010/0216909 A1 | 8/2010 | Berg et al. |
| 2010/0267554 A1* | 10/2010 | Madsen et al. ............ 504/100 |
| 2011/0053771 A1 | 3/2011 | Goodwin |
| 2011/0077155 A1 | 3/2011 | Goodwin |
| 2011/0078816 A1 | 3/2011 | Goodwin |
| 2011/0174031 A1 | 7/2011 | Bargiacchi |
| 2012/0015805 A1 | 1/2012 | Goodwin |
| 2012/0040032 A1* | 2/2012 | Miranda Valencia ........ 424/754 |
| 2012/0196747 A1 | 8/2012 | Goodwin |
| 2013/0005570 A1 | 1/2013 | Goodwin |
| 2013/0184151 A1 | 7/2013 | Hanson et al. |
| 2014/0336049 A1 | 11/2014 | Goodwin |
| 2015/0005164 A1 | 1/2015 | Hanson et al. |
| 2016/0023960 A1 | 1/2016 | Goodwin |

FOREIGN PATENT DOCUMENTS

| | | |
|---|---|---|
| CA | 2377067 A1 | 1/2001 |
| CL | 200501071 | 1/2006 |
| CN | 1111932 A | 11/1995 |
| CN | 1165801 A | 11/1997 |
| CN | 1356061 A | 7/2002 |
| CN | 1443439 A | 9/2003 |
| CN | 101148381 A | 3/2008 |
| CN | 102164493 A | 8/2011 |
| EP | 164908 | 9/1989 |
| EP | 560943 | 3/1999 |
| EP | 1216976 | 6/2002 |
| EP | 949975 | 10/2002 |
| EP | 1464635 | 10/2004 |
| EP | 1238714 | 3/2005 |
| EP | 1757187 | 2/2007 |
| EP | 23456281 | 7/2011 |
| JP | 36019500 B | 10/1961 |
| JP | 4918656 B2 | 2/1974 |
| JP | 59063102 A | 4/1984 |
| JP | 59187706 A | 10/1984 |
| JP | 63301804 A | 12/1988 |
| JP | 01164788 A | 6/1989 |
| JP | 04099413 A | 3/1992 |
| JP | 04258225 A | 9/1992 |
| JP | H04-258225 A | 9/1992 |
| JP | 05-194951 A | 8/1993 |
| JP | 07-101792 A | 4/1995 |
| JP | 10-273409 A | 10/1998 |
| JP | 2000092918 A | 4/2000 |
| JP | 2003-321290 A | 11/2003 |
| JP | 2004-513967 A | 5/2004 |
| JP | 2005-219990 A | 8/2005 |
| JP | 2006-151706 A | 6/2006 |
| JP | 2006-298724 A | 11/2006 |
| JP | 2008-501353 | 1/2008 |
| JP | 2013503898 A | 2/2013 |
| JP | 2013505892 A | 2/2013 |
| KR | 10-0835240 | 6/2008 |
| WO | WO9013420 | 11/1990 |
| WO | WO9015138 | 12/1990 |
| WO | WO9210081 | 6/1992 |
| WO | WO9517806 | 7/1995 |
| WO | WO 01-40441 A2 | 6/2001 |
| WO | WO0140441 | 6/2001 |
| WO | WO 0241903 | 5/2002 |
| WO | WO03020028 | 3/2003 |
| WO | WO03020837 | 3/2003 |
| WO | WO03094614 | 11/2003 |
| WO | WO 2004002921 A1 * | 1/2004 |
| WO | 2005000770 A1 | 1/2005 |
| WO | WO2007024753 | 3/2007 |
| WO | WO2007143791 | 12/2007 |
| WO | 2008059358 A2 | 5/2008 |
| WO | WO2009068195 | 6/2009 |
| WO | WO2009068213 | 6/2009 |
| WO | 2010006233 A2 | 1/2010 |
| WO | 2011028975 A2 | 3/2011 |
| WO | 2011038389 A1 | 3/2011 |
| WO | 2013106724 A1 | 7/2013 |

OTHER PUBLICATIONS

Masuthi, Dileepkumar A., B. S. Vyakarnahal, and V. K. Deshpande. "Influence of pelleting with micronutrients and botanical on growth, seed yield and quality of vegetable cowpea." Karnataka Journal of Agricultural Sciences 22.4 (2010).*

"Humates: Nomenclature, Sources and Quality" (Mar. 19, 2009) obtained online from URL <https://web.archive.org/web/20090319023952/http://www.bioag.com/educationandresources.html>.*

Wershaw, Robert L., "Evaluation of Conceptual Models of Natural Organic Matter (Humus) From a Consideration of the Chemical and Biochemical Processes of Humification", Scientific Investigations Report 2004-5121, US Department of the Interior, US Geological Survey (2004).

(56) References Cited

OTHER PUBLICATIONS

Pandey, Girdhar, et al., "ABR1, an APETALA2-Domain Transcription Factor that Functions as a Repressor of ABA Response in Arabidopsis", Plant Physiology, vol. 139, No. 3, pp. 1185-1193 (Nov. 2005).
http://ihss.gatech.edu/ihss2/whatarehs.html, What are Humic Substances? (Dec. 2007).
http://ihss.gatech.edu/ihss2/sources.html, Source Materials for IHSS Samples (Aug. 1, 2009).
Landec AG Inc.—Seeds of Innovation, IntelliCoat Early Plant Corn, Reference Guide.
Schulze, et al., Environment as Stress Factor: Stress Physiology of Plants, Plant Ecology, Springer, pp. 7-11 (2005).
Jonak, Claudia, et al., Stress signaling in plants: A mitogen-activated protein kinase pathway is activated by cold and drought, PNAS, vol. 93, 11274-11279 (Oct. 1996).
Zhang, Xunzhong, Influence of Plant Growth Regulators on Turfgrass Growth, Antioxidant Status, and Drought Tolerance, Dissertation. Virginia Polytechnic Institute and State.
Johnson, Kim, et al., Genetic control of plant organ growth, New Phytologist, vol. 191, 319-333 (2001).
Remus-Borel, Wilfred, et al.,"Silicon induces antifungal compounds in powdery mildew-infected wheat", Physiological and Molecular Plant Pathology, vol. 66, pp. 108-115 (2005).
Dixon et al., "Flavonoids and isoflavonoids—a gold mine for metabolic engineering," 1999, Trends in Plant Science, 4(10): 394-400.
Carbon Boost-S and FAFE-F. Datasheet (online). FBSCiences, copyright 2009-20139retrieved on Mar. 7, 2013) Retrieved from the Internet: <URL: http://www.fbsciences.com/crop-nutrition?/>.
Carbon Boost-S. Label (onlin). FBSciences, undated material (retrieved on Mar. 7, 2013) Retrieved from the Internet: <URL: http://www.fbsciences.com/kafe-f/>.
KAFE-F, KAFE-F Inproves Fertilizer Efficiencvy and Nutrient Uptake, copyright 2009-2013 (retrieved on Mar. 7, 2013) Retrieved from the Internet <URL: http://www.fbsciences.com/kafe-f/>.
Collaberative, "Humus", Wikipedia. Internet Article, Jan. 1, 2002 (retreived on Jun. 24, 2013) Retrieved from the Internet: <URL:http//en.wikipedia.org/wiki/humus/>.
Delta Farm Press "High Yields with Carbon Power Products", Jul. 23, 2009, URL: http://deltafarmpress.com/equipment/agribusiness-high-yeilds-carbon-ower-products, downloaded on Sep. 4, 2013, pp. 1-5.
FBSciences, "NPK Enhancement Products Boost Crop Yields", FBSciences News, Sep. 5, 2008, RUL:http://www.fbsadvantage.com/news/npk-enhancements-productes-boost-crop-yields/?year=2008&month=9, downloaded Aug. 4, 2013, p. 1.
Fluvic Acid Data Sheet. Datasheet [online]. ChemnetBase, 2011 [retrieved on Sep. 22, 2011], Retrived from the Internet:<http://ccd.chemnetbase.com/AAA00.entry?parentCHNumber=BFG52&exno=BFG52>, 3 pages.
Shandong Chuangxin Humic Acid Technology Co., Ltd., Humic Acid + Amino Acid Powder. <http://www.humicacidcorp.com/>, p. 1, 2009.
Shandong Chuangxin Humic Acid Technology Co., Ltd., Nitro Humic Acid. <http://www.humicacidcorp.com/>, pp. 1-2, 2009.
Steinberg, et al.."Humic Substances, Part 2: interactions with Organisisms", Environ Sci Pollut Res Int, 15(2), pp. 128-235 (2008).
WPI/Thomson, "XP-002712268", Thomson Scientific, Abstract of JP19980275483 and GB2000-311021, Apr. 4, 2000, p. 1.
Korean Intellectual Property Office, International Application No. PCT/US2013/021254 International Search Report and Written Opinion dated Apr. 29, 2013, pp. 1-14.
The International Bureau of WIPO, International Application No. PCT/US2013/021254 International Preliminary Report on Patentability dated Jul. 24, 2014, pp. 1-10.
Cacco, G., et al.;, Plant Growth Regulator Activity of Soluble Humic Complexes, Canadian Journal of Soil Science, 1984, pp. 225-228, vol. 64.
Cimrin, K. Mesut, et al.;, Phosphorus and humic acid application alleviate salinity stress of pepper seedling, African Journal of Biotechnology, 2010, pp. 5845-5851, vol. 9.
Hartwigsen, Jack A., et al.;, Humic Acid Seed and Substrate Treatments Promote Seedling Root Development, HortScience, 2000, pp. 1231-1233, vol. 35.
Turkmen, Onder, et al.; "Calcium and Humic Acid Affect Seed Germination, Growth, and Nutrient Content of Tomato (*Lycopersicon esculentum* L.) Seedlings Under Saline Soil Condition," Acta Agriculturae Scandinavica, Section B—Soil & Plant Science, 2007, pp. 168-174, vol. 54.
Schmidt, Frauke, et al.;, Molecular characterization of dissolved organic matter in pore water of continental shelf sediments, Geochimica et Cosmochimica Acta, 2009, pp. 3337-3358, vol. 73.
Sleighter, R.L., et al.; "The application of electrospray ionization coupled to ultrahigh resolution mass spectrometry for the molecular characterization of natural organic matter," Journal of Mass Spectrometry, 2007, pp. 559-574, vol. 42.
European Patent Office; Extended European Search Report for European Application No. 13735635.8 dated May 7, 2015.
Chinese Patent Office; Chinese Office Action for International Application No. 201380013974.7 dated Jul. 16, 2015; 7 pages.
Schnitzer, M., et al.; "Humic Substances in the Environment," 1972, Chapter 6, Pages 1972, Chapter 6, pp. 203-251.
Abdullah, Syamsul B., et al.; "Investigation on Aromaticity Index and Double-Bond Equivalent of Aromatic Compounds and Ionic Liquids for Fuel Desulphurization," Journal of Chemistry, 2013, pp. 1-7, vol. 2013.
Leenheer, Jerry A., et al.; "Tannins and Terpenoids as Major Precursors of Suwannee River Fulvic Acid," U.S. Geological Survey, Scientific Investigations Report 2004-5276, 2004, pp. 1-16.
Lewis, Jack Allen, "Microbial Decomposition of Vegetable Tannins and the Effect of Tannins on the Decomposition of Other Organic Materials," 1966, Rutgers—The State University, Dissertation, pp. 1-167.
Xudan, Xu, "The Effect of Foliar Application of Fulvic Acid on Water Use, Nutrient Uptake and Yield in Wheat," Australian Journal of Agricultural Research, 1986, pp. 343-350, vol. 37.
Schultz, Jack C., "Tannin-Insect Interactions," Chemistry and Significance of Condensed Tannins, R.W. Hemingway, et al., 1989, pp. 1-17.
European Patent Office; Office Action for European Patent Application No. 13735635.8 dated Mar. 29, 2016, 10 Pages.
Australian Patent Office; Office Action for Australian Patent Application No. 2013207818 dated Mar. 30, 2016, 3 Pages.
Chinese Patent Office; Office Action for Chinese Patent Application No. 201380013974.7 dated May 18, 2016, 8 Pages.
Koch, B.P., et al.; "From mass to structure: an aromaticity index for high-resolution mass data of natural organic matter," Rapid Communications in Mass Spectrometry, 2006, pp. 926-932, vol. 20.
AG Professional, "Innovative Yield Enhancement," Apr. 21, 2008, downloaded from <http://www.agprofessional.com/agprofessional-magazine/innovative_yield_enhancement_120104194.html> on Nov. 12, 2014, 2 pages.
Western Farm Press, "Floratine Biosciences (FBS) products to enhance crop nutrient uptake," Apr. 5, 2008, downloaded from <http://westernfarmpress.com/floratine-biosciences-fbs-roducts-enhance-crop-nutrient-uptake> on Nov. 12, 2014, 4 pages.
AG Professional, "Looking for Yield Response," Jan. 20, 2009, downloaded from <http://www.agprofessional.com/agprofessional-magazine/looking_for_yield_response_120089704.html> on Nov. 12, 2014, 3 pages.
USPTO; Non-Final Office Action for U.S. Appl. No. 14/371,907 dated Jan. 20, 2016, 10 Pages.
A&L Analytical Laboratories, Inc.; "How to Interpret a Soil Test Report," 2005, pp. 1-4.
Plant Management Network; "Conversion Factors for Suggested Units," APS Crop Protection and Management Collection, 2004, p. 1.

\* cited by examiner

MODULATION OF PLANT BIOLOGY

TECHNICAL FIELD

The present invention relates to compositions of matter and methods for effecting biological activity in plants. Specifically, the method comprises contacting a part of a plant or the locus thereof with a composition of matter comprising a mixture of complex polymeric polyhydroxy acids (CPPA) with added cationic species.

BACKGROUND

Various mixtures of organic compounds have been proposed in the art as fertilizer additives. Specifically, a humic acid composition, Bio-Liquid Complex™, is stated by Bio Ag Technologies International (1999) www.phelpstek.com/portfolio/humic_acid.pdf to assist in transferring micronutrients, more specifically cationic nutrients, from soil to plant.

TriFlex™ Bloom Formula nutrient composition of American Agritech is described as containing "phosphoric acid, potassium phosphate, magnesium sulfate, potassium sulfate, potassium silicate[and] sodium silicate." TriFlex™ Grow Formula 2-4-1 nutrient composition of American Agritech is described as containing "potassium nitrate, magnesium nitrate, ammonium nitrate, potassium phosphate, potassium sulfate, magnesium sulfate, potassium silicate, and sodium silicate." Both compositions are said to be "fortified with selected vitamins, botanical tissue culture ingredients, essential amino acids, seaweed, humic acid, fulvic acid and carbohydrates." See, e.g., www.horticulturesource.com/product_info.php/products_id/82. These products are said to be formulated primarily for "soilless hydrogardening" (i.e., hydroponic cultivation) of fruit and flower crops, but are also said to outperform conventional chemical fertilizers in container soil gardens. Their suitability or otherwise for foliar application as opposed to application to the hydroponic or soil growing medium is not mentioned. See www.americanagritech.com/product/product_detail.asp?ID=I&pro_id_pk=4-0.

The trademark Monarch™, owned by Actagro, LLC is a fertilizer composition containing 2-20-15 primary plant nutrients with 3% non plant food organic compositions derived from natural organic materials.

Plants in general are susceptible to a variety of environmental stresses, including for example, drought, salinity, low light, water logging, disease, pests, and temperature. Conventional nutritional plant treatments are generally unable or incapable of effecting plant biology under such conditions.

SUMMARY

Thus, in a first embodiment, a method of synergistically effecting at least one biological process in a plant is provided. The method comprising providing an aqueous mixture of: (i) an agriculturally effective amount of complex polymeric polyhydroxy acids (CPPA) having a predetermined amount of total organic carbon (TOC) and capable of positively effecting at least one biological process in a plant; and (ii) one or more of: (a) an non-agriculturally effective amount of a source of one or more transition metal cations sufficient to increase the effect of the CPPA on the biological process of the plant; and/or (b) a phytotoxic amount of at least one salt of an alkali (earth) metal salt; wherein the aqueous mixture is suitable for contacting a plant or its locus.

In a second embodiment, a composition of matter is provided. The composition of matter comprising an aqueous mixture of (i) complex polymeric polyhydroxy acids having a predetermined amount of total organic carbon (TOC); and (ii) one or more of (a) a phytotoxic amount of one or more alkali (earth) salts; and/or (b) a synergistic amount of at least one source of an agriculturally acceptable transition metal cation, wherein the mixture is at least 0.1 weight/weight transition metal cation to TOC or mixture is at least 1 to 10 weight/weight one or more alkali (earth) salts to TOC. In other aspects, the mixture is between 0.1 to 0.5 weight/weight transition metal cation to TOC, between 0.15 to 0.45 weight/weight transition metal cation to TOC, between 0.20 to 0.40 weight/weight transition metal cation to TOC, between 0.25 to 0.35 weight/weight transition metal cation to TOC, or between 0.25 to 0.30 weight/weight transition metal cation to TOC.

Granular forms and seeds contacted with the composition of matter of the second embodiment are also provided. The potent effects of the above-mentioned compositions of matter provides for wide application of these products in agriculture, horticulture, landscaping, and studies of plant biology.

DETAILED DESCRIPTION

Figure 1A:
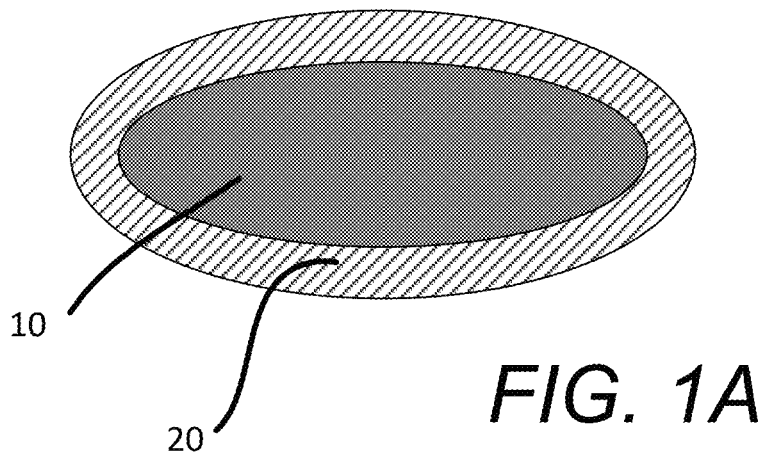
FIG. 1A. Representation of an embodiment of a seed coating according to the present disclosure.

Greenhouse and field experiments have demonstrated that CPPA (where CPPA is CAS Reg. No. 1175006-56-0), which is an alkaline extract of Complex Polymeric Polyhydroxy Acids) from organic matter, can promote plant growth and development so as to increase crop yields. Physiological studies indicate that CPPA provides improved nutrient availability and mobility inside the plants. Additionally, CPPA augments synthesis or availability of plant hormones, and/or CPPA possesses synergetic actions with some of these plant hormones. At the molecular level, plant growth and development activities are controlled and/or influenced by genes and gene expression, processes that are affected by contact with CPPA. It is likely that CPPA acts through triggering or altering the expression of critical genes involved in plant growth, development, stress tolerance, and/or disease resistance.

It has now been observed that mixtures comprising CPPA with added non-agriculturally effective amounts of transition metal salts provides synergistic effects of at least one biological process in a plant. In addition, mixtures comprising CPPA with phytotoxic amounts of alkali (earth) metal salts surprisingly provides synergistic effects of at least one biological process in a plant. Such improvement of a plant biological processes allow for improvements in agriculture and/or agronomical production.

The term "agriculturally acceptable" applied to a material or composition herein means not unacceptably damaging or toxic to a plant or its environment, and/or not unsafe to the user or others that may be exposed to the material when used as described herein.

The phrase "agriculturally acceptable source of transition metal cations" refers generally to aqueous soluble transition metal salts providing transition metal cations that are not unacceptably damaging or toxic to a plant or its environment. In particular, the phrase encompasses transition metal salts that provide a source of transition metal cations that are related to, or required for, enzymatic function, protein structure/function, and/or cellular function. Such salts include, but are not limited to, aqueous soluble salts of zinc, iron, manganese, copper, nickel, and molybdenum. Such agriculturally acceptable sources of transition metal cations encompass transition metal salts that provide a source of metal ions that are essential nutrients for plants, e.g., sometimes referred to as micronutrients.

The phrase "alkali (earth) metal" as used herein is inclusive of salts of the alkali metals and/or salts of the alkali earth metals.

The phrase "biological effect" as used herein is generally inclusive of plant processes related to or involving metal transport/metal transporters and processes that facilitate intracellular and/or intercellular transport, including mobilization (e.g., by redox chemistry), chelation, extracellular acidification, assimilatory pathways, metal loading into the xylem for root to shoot delivery, recovery of metal ions prior to leaf senescence, and intracellular distribution and/or storing of metal ions. Examples of improved "biological effects" include any increase in efficacy of a plant process to the benefit of the plant's health/vigor, yield, survival, or reproduction that otherwise would not happen under normal circumstances for the plant, such as improved germination and emergence, enhanced root and root hair growth, increased nutrient uptake and mobility in plant, mitigation of abiotic stress, improved crop quality, increased chlorophyll density, increased nodulation and nitrogen fixation (in legumes), increased yield.

The phrase "foliar surface" herein is inclusive of a leaf surface and other green parts of plants having surfaces that may permit absorption of active ingredient, including petioles, stipules, stems, bracts, flowerbuds, etc., and for present purposes "foliar surfaces" will be understood to include surfaces of such green parts.

The term "granular" and the phrase "granular form" as used herein, refers to granules, particulates, beads, and combinations thereof. For example, granular forms are those suitable for dispensing equipment commonly used in an agricultural setting. Granular forms may be of any shape or size suitable for use in an agricultural setting or in agricultural equipment.

The term "locus" as used herein is inclusive of a foliar surface and also includes an area in proximity to a plant or the area in which a plurality of seed is or can be sown.

The phrase "non-agriculturally effective amount" as used herein refers to an amount of a substance that, taken alone, has virtually no effect on a plant's biological processes, including, but not limited or related to, or required for, enzymatic function, protein structure/function, and/or cellular function. The term as used herein is inclusive of amounts at least an order of magnitude less than levels that are conventionally applied or used in agriculture. For example, a commercially available micronutrient composition of iron (Fe) typically containing about 5% iron on a wt/wt basis, with a bulk weight of about 10.7 pounds/gallon would contain about 0.535 pounds of iron, having an application rate of about 1 quart/acre, provides about 0.134 pounds of iron/acre, (or 0.294 pounds/hectare, which is about 133 grams/hectare (g/ha)). By way of contrast, a "non-agriculturally effective amount" of iron would be inclusive of about 100 milligrams iron/hectare (mg-Fe/ha) to about 500 mg iron/ha, which is an amount that is 2 to 3 orders of magnitude less than is typically used agronomically.

The phrase "phytotoxic amount" as used herein refers generally to an amount of a material or composition of matter that is toxic and/or is poisonous to a plant, regardless of the mode of action, rate, duration, or finality of the toxicity or poisoning. For example, salt water (e.g., from oceans or brackish bodies of water) contains phytotoxic amounts of one or more dissolved alkali (earth) metal salts, e.g., sodium chloride, among other compounds.

"Seed treatment" as used herein refers generally to contacting a seed with a compound or composition of matter containing or comprising at least one active ingredient (a.i. or AI). The compound or composition of matter may be in any form suitable to the seed, for example, liquid, gel, emulsion, suspension, dispersion, spray, or powder. Seed treatment is inclusive of seed coating and seed dressing. In a preferred embodiment, the A.I. is CPPA. In another preferred embodiment, the AI is a source of metal ion for the CPPA to reverse and/or improve the biological processes of the seed.

"Seed coating" or "seed dressing" as used herein refers generally to a coating or matrix formed on at least part of the seed, the coating or matrix comprising at least one AI. Optional compounds or agents may be included in the seed coating to facilitate the seed coating process or the disintegration/releasing of the at least one AI from the coating, or to prevent excessive dust-off or to add color to the treated seed.

The term "seed" as used herein, is not limited to any particular type of seed and can refer to seed from a single plant species, a mixture of seed from multiple plant species, or a seed blend from various strains within a plant species. The disclosed and described compositions can be utilized to treat gymnosperm seed, dicotyledonous angiosperm seed and monocotyledonous angiosperm seed.

The terms "synergy" and "synergistic" as used herein, generally refers to a greater than expected result that is greater than the sum of each of the effects taken separately (e.g. the effect of a combination of at least two components verses the effect of the individual components), or that the combination showed an additive result when a diminished result would have been expected. Thus, for example, the mixture of a phytotoxic material with CPPA, which would have been expected to provide a diminished effect on a biological process of a plant, is a synergistic mixture as it provided improved effects to a biological process of a plant. The combination of a non-agriculturally acceptable amount of micronutrient in combination with an amount of CPPA providing biological activity improvement to a plant greater than with either micronutrient or CPPA is inclusive of a "synergistic" combination. The amount of a component capable of providing a synergistic effect is generally referred to as a "synergistic amount."

The compositions of matter disclosed herein comprise a mixture of organic molecules isolated and extracted from sources rich in natural organic matter into an aqueous solution. The natural organic matter is primarily derived from plant materials that have been modified to varying degrees over time in a soil environment. Some of the plant materials have been recently deposited in the environment. At least a part of the natural organic matter has passed through a partial process of humification to become partially hunified natural organic matter. Humification includes microbial, fungal, and/or environmental (heat, pressure, sunlight, lightning, fire, etc.) degradation and/or oxidation of natural organic matter. Most preferably, the composition of matter contains natural organic matter that has not substantially undergone humification (partially hunified natural organic matter). In one aspect, the natural organic matter is obtained from environments typically containing or providing 5 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, or up to 500 ppm of dissolved organic matter (DOM). In other aspects, the natural organic matter is obtained from environments typically containing or providing about 500 ppm, 1000 ppm, 1500 ppm, 2000 ppm, 2500 ppm, 3000 ppm or more DOM.

Natural organic matter is extremely complex, with thousands of compounds generally present, depending upon the source and the environmental conditions prevalent about the source. The composition of matter and methods using same disclosed herein contains dissolved organic matter, the organic matter being formed during the process of humification as described above, such as microbial, fungicidal, and/or environmental (heat, pressure, sunlight, lightning, fire, etc.) degradation processes. Other natural or synthetic natural organic matter degradation processes may be involved or may be used. In one aspect, the composition of matter is best described as a complex mixture of polymeric polyhydroxy acids (hereinafter also referred to as "CPPA") that contains predominately natural organic matter that has not undergone substantial humification (e.g., partially hunified natural organic matter). The amount of humification can be determined and characterized using known methods, for example, by 13C NMR, using controls of fully or completely hunified natural organic matter, such as humic substances standards from the International Humic Substances Society, for example, Leonardite Humic Acid (LHA), Pahokee Peat Humic Acid (PPHA), and Suwannee River Fulvic Acid II (SRFA).

In one aspect, CPPA is obtained by removing a natural organic matter from its source, optionally processing, and/or concentrating to provide a CPPA composition having a dissolved organic matter (DOM) concentration level of about 10×, 25×, 50×, 100×, 200×, 300×, 400×, 500×, 600×, 700×, 800×, 900×, 1000×, 1500×, 2000×, 2500×, 3000×, 3500×, 4000×, 4500×, or 5000× (where X is "times") relative to its original source. In another aspect, CPPA concentrations of dissolved organic matter (DOM) concentration level can be about 7500×, 10,000×, 15,000×, 20,000×, 25,000×, and up to 50,000×. CPPA compositions may be adjusted such that the concentration of DOM is between about 10 ppm to about 700,000 ppm. Preferably, CPPA may be adjusted such that the concentration of DOM is between about 1000 ppm to about 500,000 ppm. CPPA compositions may be adjusted to a DOM value represented by any ppm value between 1000 ppm and 50,000 ppm, inclusive of any ppm value in 500 ppm increments (e.g., 10,500 ppm, 11,000 ppm, 11,500 ppm, 12,000 ppm, etc.) in aqueous solution. Other DOM concentrations may be used, for example, an extremely concentrated composition of between about 75,000 ppm and about 750,000 ppm can be prepared. For example, a concentrate of about 30,000× that of the original source can contain about 550,000 ppm of DOM. In certain aspects, CPPA compositions are approximately between about 91% to about 99% water, the remaining organic material being primarily DOM with minor amounts of alkali-, alkali earth-, and transition metal salts. In yet other aspects, the DOM of the CPPA composition has been dried or lyophilized in a form suitable for reconstitution with an aqueous solution. Prior to or subsequent to the processes described above, A portion of (or substantially all) of the metal ions can be removed from the CPPA to provide a CPPA product that can be adjusted to a predetermined amount or ratio of metal ion to either of the NOM or to the DOM or to the total organic carbon (TOC) of the NOM or DOM. Prior to or subsequent to the processes described above, additional metal ions can be added to the CPPA to provide a CPPA product that can be adjusted to a predetermined amount or ratio of metal ion to either of the NOM or to the DOM or the total organic carbon (TOC).

CPPA contains a complex mixture of substances, typically a heterogeneous mixture of compounds for which no single structural formula will suffice. Detailed chemical and biological testing has shown that CPPA is a unique composition both in its biological effect on plants and its chemical composition compared to Humic and Fulvic acids. Elemental and spectroscopic characterization of CPPA (and CPPA) material differentiates it from most other humic-based organic complexes, such as Humic and Fulvic Acids, as further discussed below. Blending of CPPA compositions may be performed to provide consistency of material and to compensate for the normal variations of a naturally-derived material.

Humic substances such as Fulvic Acid (CAS Reg. No. 479-66-3) and Humic Acid (CAS Reg. No. 1415-93-6) are contrasting examples of organic complexes that are derived from natural organic matter, but, as detailed below, CPPA is chemically and biologically unique from Fulvic and Humic acid. Humic substances such as Fulvic Acid and Humic Acid generally do not contain appreciable amounts of metal ions, either naturally or from processing. In some aspects, Humic substances such as Fulvic Acid and Humic Acid are useful as controls for comparison with the compositions of matter disclosed in the current application.

Characterization Methods

The organic compounds making up CPPA can be characterized in a variety of ways (e.g., by molecular weight, distribution of carbon among different functional groups, relative elemental composition, amino acid content, carbohydrate content, etc.). In one aspect, CPPA was characterized relative to known standards of humic-based substances. In another aspect, CPPA was characterized functionally to known standards of humic-based substances (standards of humic-based substances).

For purposes of characterizing carbon distribution among different functional groups, suitable techniques include, without limitation, 13C-NMR, elemental analysis, Fourier transform ion cyclotron resonance mass spectroscopy (FTICR-MS) and Fourier transform infrared spectroscopy (FTIR). The chemical characterization of CPPA and Humic substance standards were carried out using Electro spray Ionization Fourier Transform Ion Cyclotron Resonance Mass Spectroscopy (ESI-FTICR-MS), Fourier Transform Infrared Spectroscopy (FTIR) and elemental analysis for metals using ICP-AES, conducted by Huffman Laboratories, Inc. and the University of Washington.

Elemental, molecular weight, and spectroscopic characterization of CPPA is consistent with an organic complex that consists primarily of lignin and tannin compounds (and mixtures of condensed and un-condensed tannin), condensed aromatics and trace amounts of lipid and inorganics. Thousands of compounds are present, with molecular weights ranging from 225 to 700 daltons, the majority of compounds having between about 10 to about 39 carbon atoms per molecule. CPPA compositions are generally composed of carbon, oxygen, and hydrogen, with small amounts of nitrogen, and sulfur.

In one aspect the CPPA compositions disclosed herein comprise a synergistic amount of an agriculturally acceptable sources of metal ions. Thus, in one aspect, CPPA is a composition of matter comprising a metal ion content of more than 15 weight percent (w/w) to dissolved organic carbon (DOC) of the CPPA composition. In one aspect, the metal ion content in CPPA is between about 10 weight percent and about 28 weight percent of the DOC. In another aspect, the metal ion content is about 5 weight percent to about 15 weight percent of dissolved organic matter (DOM) for a CPPA composition.

The elemental composition of the dissolved solids typically present in CPPA compositions is given in Table A. If the organic compounds are separated from the inorganic compounds, the elemental breakdown is: C 55%, H 4%, O 38%, N 1.8%, and S 2.2%.

TABLE A

Average Elemental Composition of dissolved solids, based upon average values from 10 different CPPA lots (without removal of inorganic compounds).

| Element | % |
|---|---|
| Carbon | 35.1 |
| Oxygen | 24.6 |
| Hydrogen | 2.5 |
| Sulfur | 2.1 |
| Nitrogen | 1.3 |
| Potassium | 27.3 |
| Iron | 6.1 |
| Calcium | 0.2 |
| Sodium | 0.2 |
| Phosphorous | 0.1 |
| Other | 0.5 |

Among the classes of organic compounds present in CPPA, analysis generally reveals that there are lignin and tannin (mixture of condensed and un-condensed, as these terms relate to organic ring(s) structures), condensed aromatics, unidentified substances and some lipids present. In one aspect, the CPPA composition is characterized in that at least 10% of the total % compounds present in the CPPA composition is tannins and/or condensed tannins. In another aspect, the CPPA composition is characterized in that at least 15% of the total % compounds present in the CPPA composition is tannins and/or condensed tannins. In another aspect, the CPPA composition is characterized in that at least 20% of the total % compounds present in the CPPA composition is tannins and/or condensed tannins. Each of these classes of compounds is further characterized by a rather narrow Mw range and number of carbons/molecule. The breakdown of the number average and percentage of each of the various compound classes, their MW's and carbon atoms/molecule (Carbon Range) for a representative sampling of CPPA (essentially with or without metal ions) is given in Table B1.

TABLE B1

Compound Classes in CPPA along with size and carbon ranges for compounds in each class. Based upon composite of 3 different production batches. Results for individual batches are very similar.

| Compound Class | # Compounds | % of Total | Size Range (daltons) | Carbon Range |
|---|---|---|---|---|
| Lignin | 1139 | 57 | 226-700 | 11 to 39 |
| Tannin | 587 | 30 | 226-700 | 10 to 31 |
| Condensed Aromatic | 220 | 11 | 238-698 | 13 to 37 |
| Lipid | 18 | 1 | 226-480 | 14 to 30 |
| Carbohydrate | 1 | 0 | 653 | 24 |
| Other | 23 | 1 | 241-651 | 12 to 33 |

A breakdown of the number average and percentage of each of the various compound classes, their MW's and carbon atoms/molecule (Carbon Range) for a second representative sampling based upon an average of 3 different production batches (essentially with or without metal ions) for the composition of matter is given in Table B2.

TABLE B2

Compound Classes in the composition of matter, along with size and carbon ranges for compounds in each class. Based upon average of 3 different CPPA production batches. Results for individual batches are very similar.

| Compound Class | # Compounds | % of Total | Size Range (daltons) | Carbon Range |
|---|---|---|---|---|
| Lignin | 711 | 56 | 226-700 | 11 to 39 |
| Tannin | 410 | 33 | 226-700 | 10 to 31 |
| Condensed Aromatic | 122 | 10 | 238-698 | 13 to 37 |
| Lipid | 12 | ~1 | 226-480 | 14 to 30 |
| Carbohydrate | 1 | 0 | 653 | 24 |
| Other | 14 | ~1 | 241-651 | 12 to 33 |

Table C, summarizes the oxygen-to-carbon (O/C) and hydrogen-to-carbon (H/C) ratios used in defining the classes described above. In one aspect, the CPPA composition is characterized in that the O/C ratio of the dissolved organic matter present in the CPPA composition is greater than about 0.4 as measured by mass spectroscopy. In one aspect, the CPPA composition is characterized in that the H/C ratio of the dissolved organic matter present in the CPPA composition is greater than about 0.8 as measured by mass spectroscopy. In another aspect, the CPPA composition is characterized in that the H/C ratio of the dissolved organic matter present in the CPPA composition is greater than about 0.85 as measured by mass spectroscopy.

TABLE C

Elemental Ratios and chemical classifications used in characterizing CPPA samples.

| Class | O/C | H/C | Aromaticity Index |
|---|---|---|---|
| Lignin | 0.15-0.6 | 0.6-1.7 | <0.7 |
| Tannin | 0.6-1.0 | 0.5-1.4 | <0.7 |
| Condensed Aromatic | 0.1-0.7 | 0.3-0.7 | >0.7 |
| Lipid | 0-0.2 | 1.8-2.2 | |
| Carbohydrate | 0.6-1.0 | 1.8-2.2 | |

Preparation and Comparison of CPPA with Humic Substance Standards

Comparative elemental and structural characterization of Humic Substances verses CPPA was performed. Three humic substances standards from the International Humic Substances Society were used: Leonardite Humic Acid (LHA), Pahokee Peat Humic Acid (PPHA), and Suwannee River Fulvic Acid II (SRFA). Each humic substance standards and each CPPA sample was analyzed by FTIR and ESI-FTICR-MS. A portion of each humic substance standard was dissolved in water/methanol, with ammonium ions added for ionization enhancement, for the ESI-FTICR-MS analysis. Three samples of CPPA (CP#60, CPPA#75, and CPPA#99) were prepared for analysis with cation exchange resin (AG MP-50, Bio-Rad Laboratories, Hercules, Calif.) to remove metals that otherwise would interfere with the analysis. Comparison of the Humic Substance standards and each sample of the composition of matter are presented in Table D.

TABLE D

Comparison of humic substance standards and each CPPA sample.

| Sample | O/C | H/C | DBE | Avg. MW |
|---|---|---|---|---|
| Suwannee River Fulvic Acid (SRFA) | 0.39 | 1.01 | 12.7 | 445.7 |
| Pahokee Peat Humic Acid (PPHA) | 0.34 | 0.75 | 16.29 | 429.8 |
| Leonardite Humic Acid (LHA) | 0.3 | 0.79 | 15.8 | 423.6 |
| CPPA#60 | 0.54 | 0.87 | 13.7 | 472.9 |
| CPPA#75 | 0.54 | 0.89 | 13.23 | 456.9 |
| CPPA#99 | 0.5 | 0.91 | 13.23 | 455.7 |

Table D indicates that there are major differences between the Humic Substances standards and the CPPA samples. For example, the O/C ratio is less than 0.4 in all of the Humic Substances but is over 0.5 for the CPPA samples. The DBE for the CPPA samples is also significantly lower than for the Humic Acid Standards and the average MW is greater.

Based on mass spectral analysis, there are a number of compounds present in the CPPA samples that are substantially absent or greatly reduced in the Humic Substance standards. In particular, at least one component of CPPA may correspond with one or more tannin compounds. By comparison, in the Humic Substance standards, % tannin compounds are present in a small amount. For example, in the Fulvic Acid standard and in the Humic Acid standards, both standards are at least 3×-4× less than the % tannins found in the CPPA samples, as shown in Table E.

TABLE E

Number and % tannins in Humic Substance Standards verses CPPA.

| Sample | # tannins | % of tannin compounds |
|---|---|---|
| Suwannee River Fulvic Acid (SRFA) | 192 | 8.8 |
| Pahokee Peat Humic Acid (PPHA) | 9 | 1.2 |
| Leonardite Humic Acid (LHA) | 22 | 1.2 |
| CPPA#60 | 441 | 35.2 |
| CPPA#75 | 357 | 34.6 |
| CPPA#99 | 432 | 28.3 |

Comparing the Fourier Transform Infrared (FTIR) spectra for the IHSS standards and CPPA samples, there are similarities, primarily in the region from 1600 to 1800 $cm^{-1}$. In both sets of samples we see a very strong peak at around 1700 $cm^{-1}$ due to the C=O stretch from a carbonyl functional group and a peak in the 1590 to 1630 region which is consistent with a C=C bond from alkenes or aromatics. However, significant differences in the region from 700 to 1450 $cm^{-1}$ are observed. Peaks at 1160 to 1210 are present in all the spectra and are from the C—O bond of alcohols, ethers, esters and acids. The biggest difference is the peak at 870 $cm^{-1}$ in the CPPA samples, which is absent in the IHSS standards. This peak may be due to the C—H bond of alkenes and aromatics or a methoxy group.

Based on the above chemical, elemental and structural characterization, CPPA is chemically and biologically unique from Humic and Fulvic acids or combinations thereof. Further, as a result of the nature and extent of biological activity, gene regulation and over all effect of CPPA with respect to plant biology, CPPA is unique to that of known humic and/or fulvic acid compositions and treatments, for which such stress resistant activity and gene regulation properties are generally lacking in quality and quantity. Other beneficial agronomical attributes of CPPA may be present or result from the methods of treatment and/or the gene regulation obtained from CPPA.

Based on the characterization data, the CPPA may contain relatively small molecules or supramolecular aggregates with a molecular weight distribution of about 300 to about 18,000 daltons or greater. Included in the organic matter from which the mixture of organic molecules are fractionated are various humic substances, organic acids and microbial exudates. The mixture is shown to have both aliphatic and aromatic characteristics. Illustratively, the carbon distribution shows about 30-35% in carbonyl and carboxyl groups; about 30% in aromatic groups; about 18-22% in aliphatic groups, about 7% in acetal groups; and about 12% in other heteroaliphatic groups.

In some embodiments, the mixture of compounds in the CPPA comprises organic molecules or supramolecular aggregates with a molecular weight distribution of about 200 to about 30,000 daltons, for example, about 200 to about 25,000 daltons, about 200 to about 20,000 daltons, or about 200 to about 18,000 daltons.

Characterizing carbon distribution among different functional groups, suitable techniques can be used include without limitation 13C-NMR, elemental analysis, Fourier transform ion cyclotron resonance mass spectroscopy (FTICR-MS) and Fourier transform infrared spectroscopy (FTIR).

In one aspect, carboxy and carbonyl groups together account for about 25% to about 40%, for example about 30% to about 37%, illustratively about 35%, of carbon atoms in the mixture of organic compounds of the CPPA.

In another aspect, aromatic groups account for about 20% to about 45%, for example about 25% to about 40% or about 27% to about 35%, illustratively about 30%, of carbon atoms in the mixture of organic compounds of the CPPA.

In another aspect, aliphatic groups account for about 10% to about 30%, for example about 13% to about 26% or about 15% to about 22%, illustratively about 18%, of carbon atoms in the mixture of organic compounds of the CPPA.

In another aspect, acetal and other heteroaliphatic groups account for about 10% to about 30%, for example about 13% to about 26% or about 15% to about 22%, illustratively about 19%, of carbon atoms in the mixture of organic compounds of the CPPA.

In another aspect, the ratio of aromatic to aliphatic carbon is about 2:3 to about 4:1, for example about 1:1 to about 3:1 or about 3:2 to about 2:1 in the CPPA.

In a particular illustrative aspect, carbon distribution in the mixture of organic compounds of the CPPA is as follows: carboxy and carbonyl groups, about 35%; aromatic groups, about 30%; aliphatic groups, about 18%, acetal groups, about 7%; and other heteroaliphatic groups, about 12%.

Elemental composition of the organic compounds of the CPPA is independently, in one series of embodiments, as follows, by weight: carbon, about 50% to about 60%, illustratively about 55%; hydrogen, about 3% to about 5%, illustratively about 4%; oxygen, about 20% to about 30%, illustratively about 25%; nitrogen, about 0.5% to about 3%, illustratively about 1.3%; sulfur, about 0.2% to about 4%, illustratively about 2%.

Among classes of organic compounds that can be present in the CPPA are, in various aspects, amino acids, carbohydrates (monosaccharides, disaccharides and polysaccharides), sugar alcohols, carbonyl compounds, polyamines, lipids, and mixtures thereof. These specific compounds typically are present in minor amounts, for example, less than 5% of the total % of compounds. Examples of amino acids that can be present include without limitation arginine, aspartic acid, glutamic acid, glycine, histidine, isoleucine, serine, threonine, tyrosine and valine. Examples of monosaccharide and disaccharide sugars that can be present include without limitation glucose, galactose, mannose, fructose, arabinose, ribose and xylose.

Based on the above chemical, elemental and structural characterization, the CPPA is chemically and biologically unique from either Humic and Fulvic acids or their combination. Further, as a result of the nature and extent of biological inhibition of plant/seed and of gene regulation, it is generally believed that the CPPA is unique to that of known humic and/or fulvic acid compositions, for which such activity and properties are generally lacking in quality and quantity. Other agrochemical beneficial effects of plant function by the CPPA may be present or result from the methods of treatment and/or the gene regulation obtained from the CPPA.

A suitable mixture of organic compounds can be found, for example, as one of many components in products marketed as CARBON BOOST™-S soil solution and KAFE™-F foliar solution of Floratine Biosciences, Inc. (FBS). Information on these products is available at www.f-bsciences.com. Thus, exemplary compositions of aspects disclosed and described herein can be prepared by removing substantially all of the metal ions present in CARBON BOOST™-S or KAFE™-F foliar solution, for example, using an ion-exchange media and/or HPLC and adding a predetermined amount of aqueous soluble transitional metal salt. In one aspect, the active ingredient is the form of CAS Reg. No. 1175006-56-0, which corresponds, by way of example, to a representative CPPA suitable for the methods and compositions disclosed herein.

The amount of the CPPA that should be present in the composition for providing biological effect and/or gene regulation depends on the particular organic mixture used and/or the plant/soil/seed. The amount should not be so great as to result in a physically unstable composition, for example by exceeding the limit of solubility of the mixture in the composition, or by causing other essential components to fall out of solution. On the other hand, the amount should not be so little as to fail to provide biological effects, or gene regulation when applied to a target plant species or its locus. For any particular organic mixture, one of skill in the art can, by routine formulation stability and bioefficacy testing, optimize the amount of organic mixture in the composition for any particular use by following the present disclosure.

Optionally, additional components can be present in the composition of matter comprising the CPPA. For example, the composition can further comprise a second component. The second component can be of at least one agriculturally acceptable source of a plant nutrient. The second component can also be a pesticide, where the term "pesticide" herein refers to at least one herbicide, insecticide, fungicide, bactericide, anti-viral, nematocide, or a combination thereof.

Methods of use of the CPPA composition as described herein for positively effecting one or more biological effects of a plant are further disclosed. The composition can be applied to a single plant/seed (e.g., a houseplant or garden ornamental) or to an assemblage of plants occupying an area. In some embodiments, the composition is applied to an agricultural or horticultural crop, more especially a food crop. A "food crop" herein means a crop grown primarily for human consumption. Methods of the present invention are appropriate both for field use and in protected cultivation, for example, greenhouse use.

While the present methods can be beneficial for gramineous (belonging to the grass family) crops such as cereal crops, including corn, wheat, barley, oats and rice, they are also highly appropriate for non-gramineous crops, including vegetable crops, fruit crops, broad-leaved field crops such as soybeans, seed crops or a crop of any species grown specially to produce seed. The terms "fruit" and "vegetable" herein are used in their agricultural or culinary sense, not in a strict botanical sense; for example, tomatoes, cucumbers and zucchini are considered vegetables for present purposes, although botanically speaking it is the fruit of these crops that is consumed.

Vegetable crops for which the present methods can be found useful include without limitation:

leafy and salad vegetables such as amaranth, beet greens, bitterleaf, bok choy, Brussels sprout, cabbage, catsear, celtuce, choukwee, Ceylon spinach, chicory, Chinese mallow, chrysanthemum leaf, corn salad, cress, dandelion, endive, epazote, fat hen, fiddlehead, fluted pumpkin, golden samphire, Good King Henry, ice plant, jambu, kai-lan, kale, komatsuna, kuka, Lagos bologi, land cress, lettuce, lizard's tail, melokhia, mizuna greens, mustard, Chinese cabbage, New Zealand spinach, orache, pea leaf, polk, radicchio, rocket (arugula), samphire, sea beet, seakale, Sierra Leone bologi, soko, sorrel, spinach, summer purslane, Swiss chard, tatsoi, turnip greens, watercress, water spinach, winter purslane and you choy;

flowering and fruiting vegetables such as acorn squash, Armenian cucumber, avocado, bell pepper, bitter melon, butternut squash, caigua, Cape gooseberry, cayenne pepper, chayote, chili pepper, cucumber, eggplant (aubergine), globe artichoke, luffa, Malabar gourd, parwal, pattypan squash, perennial cucumber, pumpkin, snake gourd, squash (marrow), sweetcorn, sweet pepper, tinda, tomato, tomatillo, winter melon, West Indian gherkin and zucchini (courgette);

podded vegetables (legumes) such as American groundnut, azuki bean, black bean, black-eyed pea, chickpea (garbanzo bean), drumstick, dolichos bean, fava bean (broad bean), French bean, guar, haricot bean, horse gram, Indian pea, kidney bean, lentil, lima bean, moth bean, mung bean, navy bean, okra, pea, peanut (groundnut), pigeon pea, pinto bean, rice bean, runner bean, soybean, tarwi, tepary bean, urad bean, velvet bean, winged bean and yardlong bean;

bulb and stem vegetables such as asparagus, cardoon, celeriac, celery, elephant garlic, fennel, garlic, kohlrabi, kurrat, leek, lotus root, nopal, onion, Prussian asparagus, shallot, Welsh onion and wild leek;

root and tuber vegetables, such as ahipa, arracacha, bamboo shoot, beetroot, black cumin, burdock, broadleaf arrowhead, camas, canna, carrot, cassava, Chinese artichoke, daikon, earthnut pea, elephant-foot yam, ensete, ginger, gobo, Hamburg parsley, horseradish, Jerusalem artichoke, jicama, parsnip, pignut, plectranthus, potato, prairie turnip, radish, rutabaga (swede), salsify, scorzonera, skirret, sweet potato, taro, ti, tigernut, turnip, ulluco, wasabi, water chestnut, yacon and yam; and herbs, such as angelica, anise, basil, bergamot, caraway, cardamom, chamomile, chives, cilantro, coriander, dill, fennel, ginseng, jasmine, lavender, lemon balm, lemon basil, lemongrass, marjoram, mint, oregano, parsley, poppy, saffron, sage, star anise, tarragon, thyme, turmeric and vanilla.

Fruit crops for which the present methods can be found useful include without limitation: apple, apricot, banana, blackberry, blackcurrant, blueberry, boysenberry, cantaloupe, cherry, citron, clementine, cranberry, damson, dragonfruit, fig, grape, grapefruit, greengage, gooseberry, guava, honeydew, jackfruit, key lime, kiwifruit, kumquat, lemon, lime, loganberry, longan, loquat, mandarin, mango, mangosteen, melon, muskmelon, orange, papaya, peach, pear, persimmon, pineapple, plantain, plum, pomelo, prickly pear, quince, raspberry, redcurrant, starfruit, strawberry, tangelo, tangerine, tayberry, ugli fruit and watermelon.

Seed crops for which the present methods can be found useful include without limitation: specialized crops used to produce seed of any plant species, for which the present methods can be found useful include, in addition to cereals (e.g., barley, corn (maize), millet, oats, rice, rye, sorghum (milo) and wheat), non-gramineous seed crops such as buckwheat, cotton, flaxseed (linseed), mustard, poppy, rapeseed (including canola), safflower, sesame and sunflower.

Other crops, not fitting any of the above categories, for which the present methods can be found useful include without limitation sugar beet, sugar cane, hops and tobacco.

Each of the crops listed above can have its own particular biological effect needs. Further optimization of compositions described herein for particular crops can readily be undertaken by those of skill in the art, based on guidance provided in the present disclosure, without undue experimentation.

Methods of using the compositions disclosed and described herein for positively effecting plant biology comprise applying a composition as described herein to a seed, to a foliar surface of a plant, or to a locus of the plant or seed. Such methods provide, among other agricultural benefits, include any increase in efficacy of a plant process to the benefit of the plant's health/vigor, yield, survival, or reproduction that otherwise would not happen under normal circumstances for the plant, such as improved germination and emergence, enhanced root and root hair growth, increased nutrient uptake and mobility in plant, mitigation of abiotic stress, improved crop quality, increased chlorophyll density, increased nodulation and nitrogen fixation (in legumes), and/or increased yield, compared to plants not treated with the compositions described and disclosed herein.

Compositions disclosed and described herein can be applied using any conventional system for applying liquid or solid to a seed or foliar surface or its locus. Most commonly, application by spraying will be found most convenient, but other techniques, including application by injection, tumbling, brush or by rope-wick, drizzle between rows, in-furrow, shank, and the like, can be used if desired. For spraying, any conventional atomization method can be used to generate spray droplets, including hydraulic nozzles and rotating disk atomizers. Introduction of the composition into an irrigation system can be used.

For foliage surface or locus applications, the application rate of the composition can be between about 0.001 gram/ha to about 100.0 gram/ha dry weight, between about 0.2 gram/ha to about 2.0 gram/ha dry weight, between 0.3 gram/ha to about 1.5 gram/ha dry weight, or between about 0.4 gram/ha to about 1.0 gram/ha dry weight applied in the soil or as a foliar application to the foliage or the locus of the plant.

Compositions disclosed and described herein can be provided in concentrate form, (e.g., liquid, gel, or reconstitutable powder form), suitable for further dilution and/or mixing in water prior to application to the seed, plant, or locus. Alternatively, they can be provided as a ready-to-use solution for direct application. Because compositions disclosed and described herein can be combined with other fertilizer solutions and/or with pesticide solutions, they can be diluted and/or reconstituted by mixing with such other solutions.

The above concentrate compositions are suitable for further dilution. For application to plant foliage, a concentrate composition can be diluted up to about 600-fold or more with water, more typically up to about 100-fold or up to about 40-fold. Illustratively, a concentrate product can be applied at about 0.1 to about 3.0 L/ha, for example about 5 to about 2.5 L/ha, in a total application volume after dilution of about 60 to about 600 L/ha, for example about 80 to about 400 L/ha or about 100 to about 200 L/ha.

For seed treatment applications, a concentrate composition can be diluted up to about 600-fold or more with water, more typically up to about 100-fold or up to about 40-fold. Illustratively, a concentrate product can be applied at about 0.1 mg/Kg seed to about 100 mg/Kg seed, for example about 0.1 mg/Kg seed, 0.5 mg/Kg seed, 0.75 mg/Kg seed, 1.0 mg/Kg seed, 1.25 mg/Kg seed, 1.5 mg/Kg seed, 1.75 mg/Kg seed, 2.0 mg/Kg seed, 2.5 mg/Kg seed, 3.0 mg/Kg seed, 3.5 mg/Kg seed, 4.0 mg/Kg seed, 4.5 mg/Kg seed, 5.0 mg/Kg seed, 5.5 mg/Kg seed, 6.0 mg/Kg seed, 6.5 mg/Kg seed, 7.0 mg/Kg seed, 7.5 mg/Kg seed, 8.0 mg/Kg seed, 8.5 mg/Kg seed, 9.0 mg/Kg seed, 9.5 mg/Kg seed, and 10.0 mg/Kg seed. A concentrate product can also be applied at about 15 mg/Kg, 20 mg/Kg, 25 mg/Kg, and 30 mg/Kg.

Application solutions prepared by diluting concentrate compositions as described above represent further aspects of the compositions and methods disclosed and described herein.

Experimental

Figure 6:
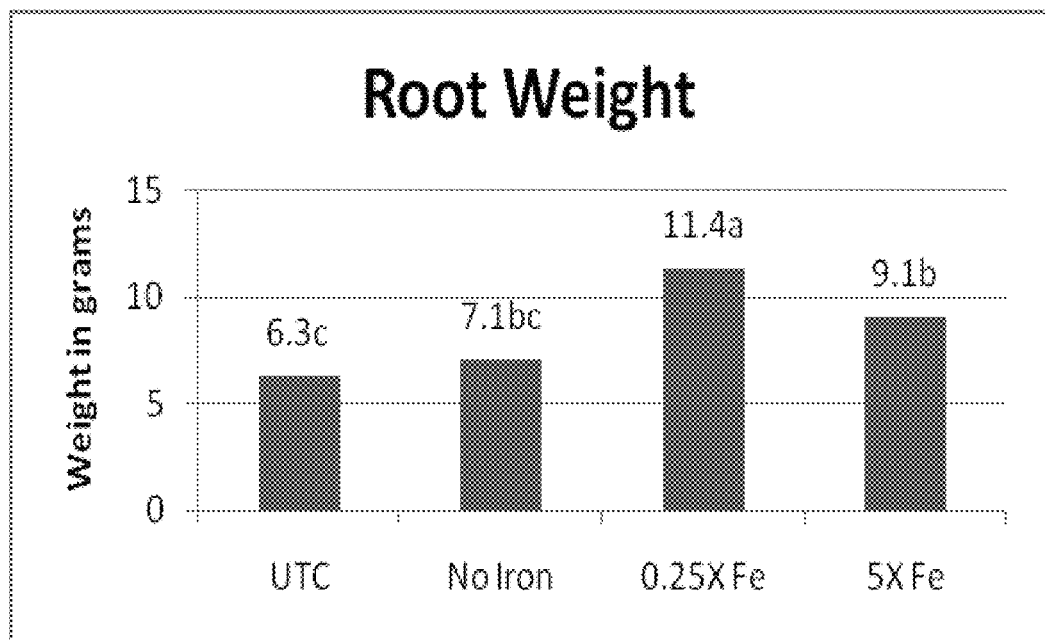

Seed Coatings As depicted in FIG. 6, seed coatings and/or seed dressings comprising a seed 10 and a first layer 20 at least partially surrounding the seed 10 is provided. First layer 20 comprises an effective amount of CPPA so as to positively effect a biological process of the seed. The CPPA can be contained in a polymer or other matrix that is configured for controlled degradation after sowing. Suitable polymers or matrixes include hydrogels, microgels, or sol-gels. Specific materials and methods of coatings seeds useful in this regard include such process and materials as used, for example, Intellicoat™ (Landec Inc., Indiana); Thermo-Seed™ (Incotec, Netherlands) CelPril™ (Bayer Crop-Science); ApronMaxx™ (Syngenta); and Nacret™ (Syngenta). The CPPA, NOM, or other AI's ("actives") can be provided and incorporated into the polymer or matrix, or directly adhered to the seed coat. The thickness of the polymer or matrix coating may be between from about 0.01 mils to about 10 mils in thickness. The polymer or matrix can be designed to release the actives in response to temperature, moisture content, sunlight, time, or combinations thereof. The polymer or matrix can quickly dissolve or disintegrate releasing the actives or can controllable release the actives over time or in response to a predetermined condition such as temperature, moisture content, sunlight, time, or combinations thereof. The polymer or matrix can be multi-layer, with discrete layers, for example, for disrupting the coating to allow moisture ingress, housing the actives, etc. In this configuration additional layers can be positioned in-between the seed and the CPPA for example, an amount of agriculturally acceptable transition metal cations sufficient to increase the biological process effect of the CPPA on the plant, or a phytotoxic amount of a salt of an alkali (earth) metal salts. First layer 20 and any additional intervening layers can be configured for controlled degradation such that the positive biological effect is delayed after sowing. Additional agrochemical AI's as discussed above can be added to the CPPA material in the first layer 20 and/or an intervening layer. The introduction of CPPA and/or the metals or salt can be reversed as described above.

Figure 1B:
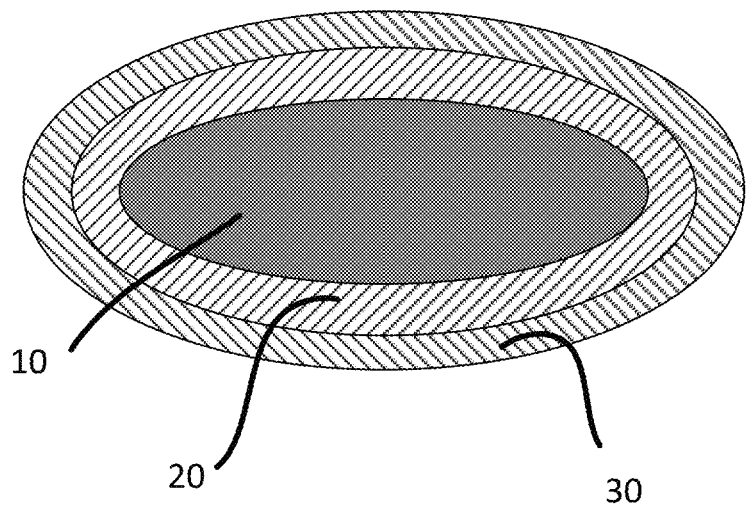
FIG. 1B Representation of another embodiment of a seed coating according to the present disclosure.

As depicted in FIG. 1, seed coatings and/or seed dressings comprising a seed 10 and a first layer 20 at least partially surrounding the seed 10 and second coating 30 is provided. First layer 20 comprises an effective amount of CPPA so as to inhibit seed germination for a predetermined time. The CPPA can be contained in a polymer or other matrix as described above that is configured for controlled degradation after sowing. In this configuration additional layers can be positioned in-between the seed and the CPPA. These additional intervening layers can also be configured for controlled degradation such that the positive biological effect is delayed for a time after sowing. Second layer 30 comprises an effective amount of metal ions and/or salt so as to provide the positive (or synergistic) biological effects when combined with the CPPA of first layer 20. Second layer 30 can comprise a polymer or other matrix that is configured for controlled degradation at a predetermined time after sowing. Additional, intervening layers can be positioned in-between the first layer 20 and the second layer 30. These additional intervening layers can also be configured for controlled degradation such that the release of metal ions and/or salt is delayed after sowing for a predetermined time. Additional agrochemical AI's as discussed above can be added to the first layer 20, the second layer 30, and/or an intervening layer(s). Additional layers, coloring, powders, and the like can be applied or used for the coated seeds. The coated seeds can then be sown to increase the seed's biological process and/or to first delay and then increase or improve the seed's biological process.

Coated Granular Forms for Soil and/or Locus Application

In one aspect, a granular form is contacted with an aqueous solution or powder of the CPPA to provide a composition of matter for providing positive effects on a plant's biological process for a first predetermined time that can be following by the introduction of a fertilizing material at a second predetermined time. In one aspect, the composition of matter provides a controlled or delayed release form of the CPPA. Suitable granular forms can be clays and include, for example, montmorillonite, allapulgite, and hydrous aluminosilicate minerals. Montmorillonite mineral is from the non-swelling bentonite class of clays (e.g., from Ripley, Miss. and Mounds, Ill.). Montmorillonite has a low bulk density and high absorbtivity which allows higher liquid holding capacity of aqueous solutions of the CPPA. Attapulgite mineral, also known as Fuller's earth, is also from the non-swelling bentonite class and is obtained from Ochlocknee, Ga. Attapulgite's low bulk density and high absorbtivity allows higher liquid holding capacity of aqueous solutions of the CPPA. Hydrous aluminosilicate also has a low bulk density and high absorbtivity allowing for higher liquid holding capacity of aqueous solutions of the CPPA. Suitable clay granular forms for use with the CPPA as disclosed herein are available from Oil-Dri Corp. (Alpharetta, Ga.). The clay granule's micropore structure is adjusted to optimize the absorption and/or optimize release and/or optimize environmental stability of the CPPA for use in agriculture.

Figure 2A:
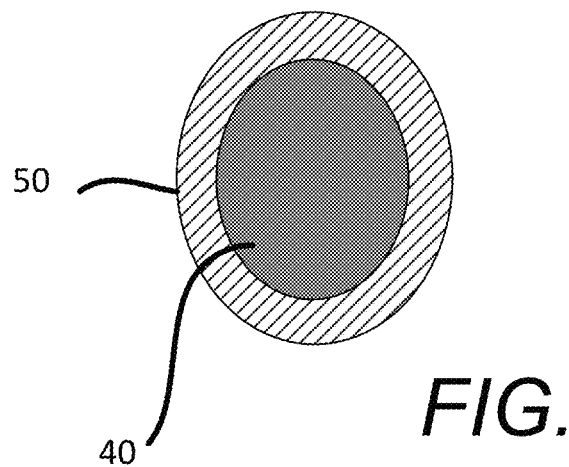
FIG. 2A. Representation of another embodiment of a coated granular form according to the present disclosure.
Figure 2B:
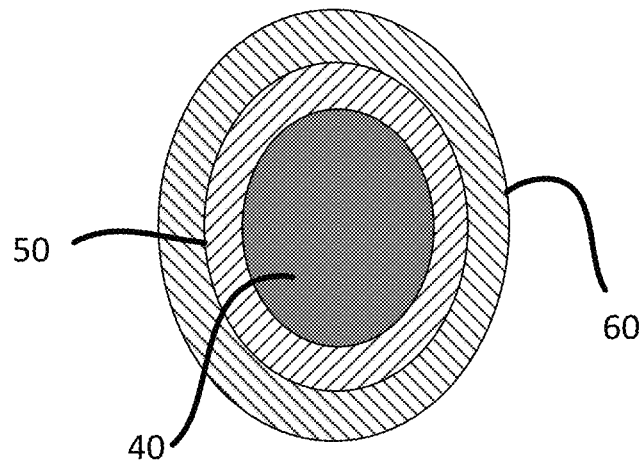
FIG. 2B. Representation of another embodiment of a coated granular form according to the present disclosure.

As depicted in FIG. 2A, granular forms 40 and a first layer 50 at least partially surrounding the granular form 40. FIG. 8 depicts a second aspect of the granular form coated with first layer 50 and second coating 60. First layer 50 comprises an effective amount of metal ions, for example, an amount sufficient to cease or reverse the inhibition of a plant biological process. The metal ions can be contained/impregnated in a polymer or other matrix as described above that is configured for controlled degradation. While the term "layer" is used in reference to FIG. 2B, the metal ions or salt can be included in the granular form with or without a physical "layer" on the granular form. Second layer 60 comprises an effective amount of CPPA so as to positively effect a plant biological process. The CPPA can be contained in a polymer or other matrix as described above that is configured for controlled degradation. In this configuration additional layers can be positioned in-between the granular form and the metal free CPPA composition of matter. These additional intervening layers can also be configured for controlled degradation such that the positive effect is delayed for a predetermined time. In this configuration the positive effect (or synergistic effect) can be concurrent or followed by an increase or improvement of a biological process upon re-introduction of metal ions to the CPPA. Additional, intervening layers can be positioned in-between the first layer 50 and the second layer 60. These additional intervening layers can also be configured for controlled degradation such that the release of metal ions or salt is delayed for a predetermined time. Additional agrochemical AI's as discussed above can be added to the first layer 50, the second layer 60, and/or an intervening layer. Additional layers, colorants, processing aids, powders, and the like can be applied or used. The introduction of CPPA and/or the metals or salt can be reversed as described above.

The relative surface pH of the particular clay granule may be acidic or basic, for example, between about 3 to about 11. The relative surface pH of the clay granule may be chosen to control the release of the CPPA and/or improve long-term bioavailability and/or delay release of an effective amount of the CPPA after application to the locus of a seed or plant. For example, clay granules with a relatively acidic surface chemistry typically have slower degradation and release properties than clay granules with a relatively basic surface chemistry. Application of the CPPA to a clay granular form of relatively acidic surface pH can provide for long-term bioavailability of the CPPA with little or no loss in the efficacy while providing for the delayed release of an effective amount of the CPPA as compared to direct soil application of the CPPA.

In certain aspects, slow release granules having a pH of about 4 to about 6 with the CPPA and metal and/or salt can be used to improve sown seed and/or plant health, growth or pest-resistance and or the delayed release of an effective amount of the CPPA. In other aspects, combinations of fast release clay granules having a pH of about 9 to about 10 and slow release granules having a pH of about 4 to about 6 with the CPPA are used to improve the health, growth, or pest-resistance of a sown seed and/or plant. Such combinations of acidic/basic granular forms provides for essentially the immediate release of an effective amount of the CPPA and metal and/or salt followed by the delayed release of an effective amount of the CPPA at a predetermined latter time.

In one aspect, the CPPA can be sprayed onto the clay granules and/or first layer 50 and dried. In another aspect, the clay granules with or without first layer 50 can be tumbled with the CPPA, or a fluidized bed may be used. The treated clay granular form can then be applied to the locus of a sown seed and/or plant to improve the plant biological process.

In another aspect, the clay granular form may be applied to the locus of a sown seed or a plant and the CPPA can be applied essentially to the same locus, whereas at least a portion of clay granulate will be contacted with the CPPA to provide essentially an instant release of an effective amount of the CPPA to the soil and/or foliage, followed by the delayed release of an effective amount of the metal and/or salt to the locus at a predetermined latter time to provide an enhancement of the effect provided by the instantly released CPPA.

In one aspect, the clay granular form is contacted with the CPPA combined with, or sequentially contacted by, a second component to provide a subsequent treatment for improved health, growth or stress-resistance of a sown seed or plant. In another aspect, the clay granular form can be contacted with the CPPA or at least one second component in sequential order to maximize the effectiveness of either component or to minimize interactions of the components and/or the clay granular form.

In one aspect, the clay granular form contacted with the CPPA and optionally the second component is applied to the locus essentially simultaneously with the seed, for example, as the seed is sown or after emergence of the plant.

Granular Forms of Urea with CPPA

In one aspect, the granular form comprises urea. The granular urea with or without first coating 50 is contacted with the CPPA to provide a composition of matter of manufacture suitable for agricultural use. In one aspect, the granular form is a Sulfur-Coated Urea (SCU) or a Polymer-Coated Urea (PCU or ESN), herein after collectively referred to as urea granular form.

Sulfur-Coated Urea (SCU) is a controlled-release nitrogen fertilizer typically providing a NPK analysis of about 25-0-0 to about 38-0-0, and about 10-30% sulfur. SCU's typically are designed such that a quick-releasing form of nitrogen (such as urea) is provided for fast green-up and immediate feeding and a slow-release form are provided for longer-lasting nourishment.

SCU sulfur-coated urea granular form can be prepared in a number of ways, typically by spraying preheated urea granules with molten sulfur and optionally a wax. The thickness of the sulfur coating can be controlled for optimizing handling, in-loading, shipping, blending and bagging and to reduce premature break down and release of all the nitrogen at one time. SCU granules are available commerically in different granular sizes. Suitable SCU include, for example, Nu-Gro Technologies SCU® (Ontario, Canada).

In one aspect, the CPPA can be sprayed onto the SCU granules with or without first coating 50 and dried. In another aspect, the SCU granules with or without first layer 50 can be tumbled with the CPPA, or a fluidized bed may be used. The treated SCU granules can then be applied to the locus of a sown seed and/or plant to improve its health, growth or pest-resistance. In another aspect, the SCU granular form may be applied to the locus of a sown seed or a plant and the CPPA can be applied essentially to the same locus, whereas at least a portion of SCU granular form will be contacted with the CPPA to provide essentially an instant soil and/or foliage treatment of an effective amount of the CPPA and a delayed release of an effective amount of either the metal ions or salt, or other AI to the locus at a predetermined latter time.

Coating urea with sulfur and subsequent contact with the CPPA provides for controlled-release of a nitrogen source and a sulfur source post-inhibition after contact with the CPPA so as to cease, restore and/or improve improved health, growth or stress-resistance of a sown seed or plant. In one aspect, the sulfur-coated urea contacted with the CPPA can provide for inhibition of a biological process of a sown seed or plant essentially immediately, and/or then provide for fertilizing continuing up to about eight, nine, ten, eleven, or to about 12 weeks or more post-application, depending on environmental conditions.

In one aspect, the CPPA is combined with an additional AI and the combination is contacted with the SCU granulate to provide a treatment for improved health, growth or stress-resistance of a sown seed or plant. In another aspect, the SCU particulate can be contacted with the CPPA or at least one second component in sequential order to maximize the effectiveness of either component or to minimize interactions of the components and/or the SCU particulate.

Polymer Coated Urea Treated with CPPA

In one aspect, a Polymer-Coated Urea (PCU or ESN) granulate is contacted with the CPPA to provide a controlled release form of the CPPA in combination with a fertilizer. Polymer-Coated Urea (PCU or ESN) is a controlled-release nitrogen fertilizer typically providing a NPK analysis similar to a SCU without the sulfur. PCU's typically are designed such that a quick-releasing form of nitrogen (such as urea) is provided for fast green-up and immediate feeding and a slow-release form are provided for longer-lasting nourishment. The metal ion layer 50 can be used or the metal ions can be incorporated in the polymer coating the urea granular form.

PCU-coated urea can be prepared in a number of ways, typically by spraying urea granules with polymer solutions and drying. The thickness of the polymer coating can be controlled for optimizing handling—in loading, shipping, blending and bagging and to modify or adjust the release rate of the urea. For example, the release rate of the urea may be controlled by adjusting the polymer chemistry and/or polymer coating thickness. Polymer coating chemistry can be adjusted to control release of urea based on temperature and/or moisture. The polymer coating may be biodegradable or remain intact during or after urea release. Suitable PCU include, for example, POLYCON, ESN® Smart Nitrogen (Agrium Inc., Calgary, Canada).

In one aspect, the CPPA and the metal ion or salt containing layer can be sprayed onto the PCU granulate and dried. In another aspect, the PCU granulate with the first layer 50 can be tumbled with the CPPA, or a fluidized bed may be used. The CPPA can form a coating on the first layer 50, the polymer, penetrate the polymer coating, or all of these. In one aspect, the CPPA can be mixed or otherwise dispersed or blended with the polymer prior to coating the urea granulate.

In another aspect, the PCU granular form may be applied to the locus of a sown seed or a plant and the CPPA can be applied essentially to the same locus, whereas at least a portion of PCU granular form will be contacted with the CPPA to provide essentially an instant soil and/or foliage treatment of an effective amount of the CPPA and a delayed release of an effective amount of the CPPA or metal ion or salt to the locus at a predetermined latter time.

In another aspect, the CPPA is combined with another AI and the combination is contacted with the PCU granulate (or mixed with the polymer coating prior to coating of the urea particulate) to provide a treatment for improved health, growth or stress-resistance of a sown seed or plant. In another aspect, the PCU particulate can be contacted with the CPPA or at least one second component in sequential order to maximize the effectiveness of either component or to minimize interactions of the components and/or the PCU particulate.

Polymer coating urea with a polymer containing the CPPA or subsequent contact of the polymer coated urea with the CPPA provides for controlled-release of a nitrogen source in combination with the CPPA for improved health, growth or stress-resistance of a sown seed or plant. Typically, polymer-coated urea contacted with the CPPA can provide for improving a plant biological process and/or improving the health, growth or stress-resistance of a sown seed or plant essentially immediately thereafter, continuing up to about eight, nine, ten, eleven, or to about 12 weeks or more post-application, depending on environmental conditions. A sustained, controlled release of and nitrogen in combination with the CPPA provides for the enhanced uptake of other nutrients essential for growth, and disease resistance. The controlled-release composition comprising the PCU contacted with the CPPA can reduce the total number of applications and/or prevent plant injury.

In another aspect, the urea granular form (SCU or PCU) is used in combination with the clay granular form disclosed above, provided that at least one of the granular forms are contacted with the CPPA either initially or subsequently to application to a locus, to provide a controlled release form of an effective amount of the CPPA and metal ion or salt, in combination with a fertilizer. Such combinations of clay granular forms and urea granular forms can provide essentially an instant of an effective amount of the CPPA to the locus with fertilizer, and a delayed release to the soil and/or foliage of an effective amount of SCU or PCU at a predetermined latter time.

Other forms of urea may be sulfur- or polymer-coated, substituted for, or combined with SCU for the practice of the disclosure herein, including coated or uncoated granular forms of urea formaldehyde (UF) and/or methylene urea (MU), for example, Formolene, FLUF, Nitro 26 CRN, Nitroform, or CoRoN. The releasing properties of the UF and MU may be controlled by adjusting the N-C-N chain length of the material. Various types of cold water soluble nitrogen (CWSN), cold water insoluble nitrogen (CWIN) and hot water insoluble nitrogen (HWIN) forms of urea and combinations thereof may be used. Isobutylene diurea (IBDU) may be used. Various processing aids may be used to assist contacting the CPPA with the clay or urea granular form. Such processing aids include penetrants such as dimethylsufoxide (DMSO), alcohols, oils, tackifiers, emulsifiers, dispersants, adhesion promoters, defoamers, etc, as are generally known and practiced. Processes for preparing a composition disclosed and described herein typically involve simple admixture of the components and the granular form. Order of addition is not generally critical. In one aspect, the amount of CPPA applied to the granule is chosen such that an amount of granule sufficient to uniformly cover a locus of sown seed or plant using dispensing equipment is provided. Such amounts of CPPA as a.i. relative to the weight of granular form is readily determined without undue experimentation by any person skilled in the art or by following the exemplary disclosure set forth in this application.

Methods

Methods of use of the composition as described herein for soil and/or foliage treatment providing positive improvement or synergistic improvement of a biological process of a plant are further disclosed with reference to FIGS. 1-2. The granular forms (clay, SCU, PCU, etc.) with or without first layer 50 treated with a composition comprising at least CPPA or NOM, optionally with at least one second component (herein after referred to as "treated granular form") can be applied to a single plant (e.g., commercial crop, a houseplant, or garden ornamental), to an assemblage of plants occupying an area, or to a locus of sown seed or plant. The treated granular form can be combined with seed as the seed is introduced into or on soil or other growing media, or the treated granular form can be applied to the locus after sowing, or to the locus of emerged plants.

Experimental Section

General. In the corresponding Figures and tables, means of the samples are presented, and means followed by same letter do not significantly differ (P=0.05, Duncan's New MRT). In the experiments, an untreated check ("UTC") was a treatment with only water. The term "about" can be read to provide an inclusive range equivalent to an encompassing normal error in the method or manner of determining the particular numerical value, e.g., experimental error, equipment error, or averaging. In the alternative, "about" is inclusive of +/−10 percent of the stated numeric value.

Transition Metal Salts in Combination with CPPA

Adding iron ions (e.g., with FeSO4) back to CPPA treated with a cation exchange resin (metal-free CP) significantly improved biological responses in plants. In general, the Fe free CPPA performed poorly compared to the UTC. When Fe was added (e.g., as FeSO4), there was a significant positive biological plant response superior to that of the UTC and the metal-free CPPA. The plant biological response was generally observed to be better when a stoichiometric amount of Fe was added back (relative to the amount of CPPA or its TOC value) rather than an excess amount.

Removing essentially all of the aqueous soluble iron (Fe) from the CPPA negatively impacts germination and root development. However, removing Fe from the CPPA does not seem to impact shoot development. Treating seeds with Fe alone appears to have a negative effect on root development and on shoot development. When Fe is added to CPPA having been previously treated with the cation exchange resin so as to remove essentially all of the aqueous soluble Fe, the results for root development are essentially that of the original untreated CPPA, within statistical error. When CPPA with the iron removed is added to a $FeSO_4$ solution, the CPPA appears to compensate for the negative effects of the $FeSO_4$ alone on shoot development. These observations support the premise that the combination of CPPA and Fe are synergistic in their interaction and biological effect on plants and/or seeds.

The purpose of these experiments were to determine the biological effect on plants of the presence or absence of an aqueous soluble iron salt (Fe) in a CPPA composition, and the biological effect on plants upon the addition of an excess added amount of Fe to a CPPA composition.

Experiment Fe-1: Foliar Treatment of CPPA/Fe Compositions—The purpose of this experiment was to determine the biological effect on plants in the presence or absence of an added aqueous soluble iron salt (Fe) added to a CPPA composition. Thus, tomato plants (Lycopersicon es.) were produced from seed and transplanted into 3 inch by 3 inch pots for this experiment. There were four treatments in total with 10 replicates per treatment arranged in a Randomized Complete Block design. All pots received an application as a foliar spray 18 days after transplanting. The untreated check (UTC) was a treatment with only water. All test pots were treated with the CPPA/Fe compositions at a rate equivalent so as to achieve 520 mg of organic carbon per hectare. Samples were prepared by first removing the iron from a CPPA composition (iron-free CPPA composition) by use of a cation exchange resin (AG MP-50 Resin, Bio-Rad Laboratories, 2000 Alfred Nobel Drive, Hercules, Calif. 94547) and then adding back to the iron free CPPA composition appropriate amounts of $FeSO_4$ to provide two test samples of known Fe wt. %, one at about 25% w/w of the total organic carbon, or so as to provide 130 mg of Fe per hectare (hereafter "0.25× Fe"), and a second at an amount 5 times the carbon on a w/w basis, or so as to provide about 2.6 g of Fe per hectare (hereafter "5× Fe"). Fourteen days after application, the plants were measured for vigor, the number of leaves per plant, total plant weight, root, and shoot weights. Graphs of the data are shown in FIGS. 3-7.

Figure 3:
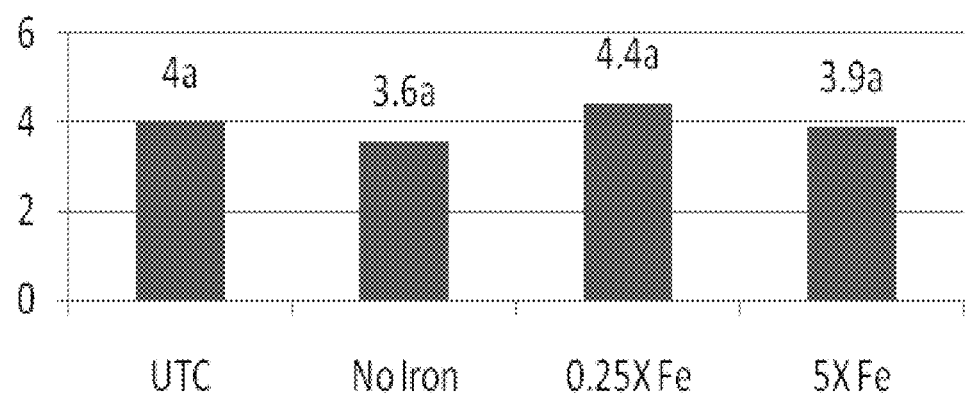
FIGS. 3-7. Graphical representations of biological response observed for plant vigor, leaves per plant, plant weight, plant root weight, and plant shoot weight, respectively, verses control, after treatment with compositional embodiments of the present disclosure.
Figure 4:
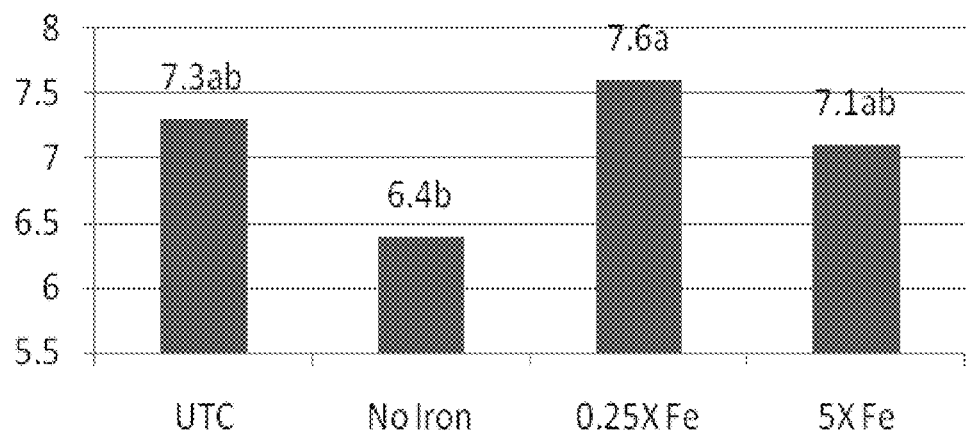
Figure 5:
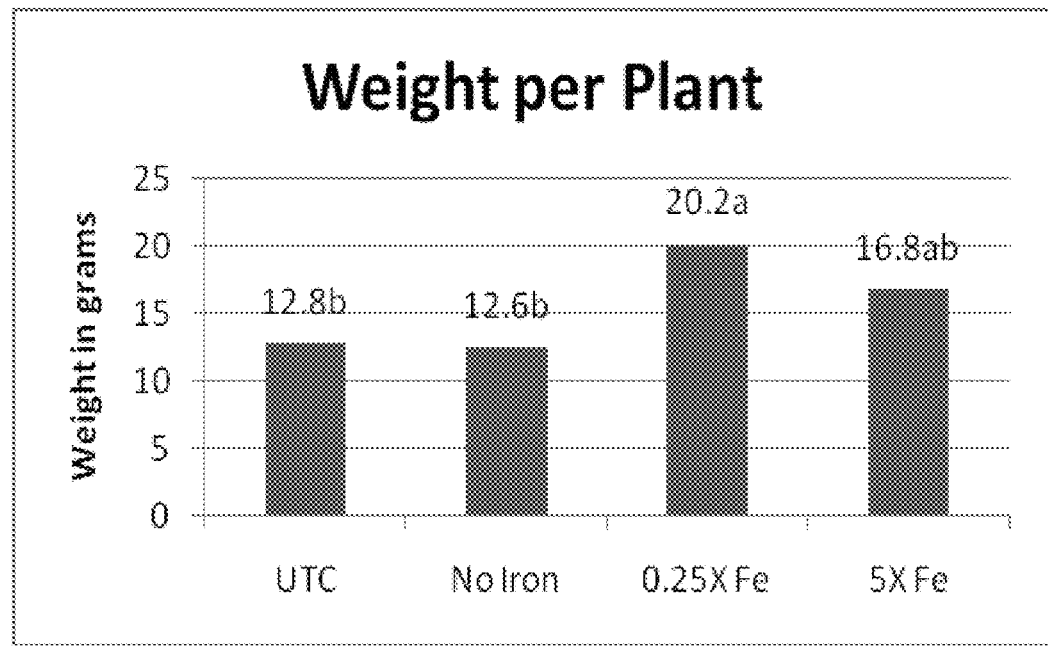
Figure 7:
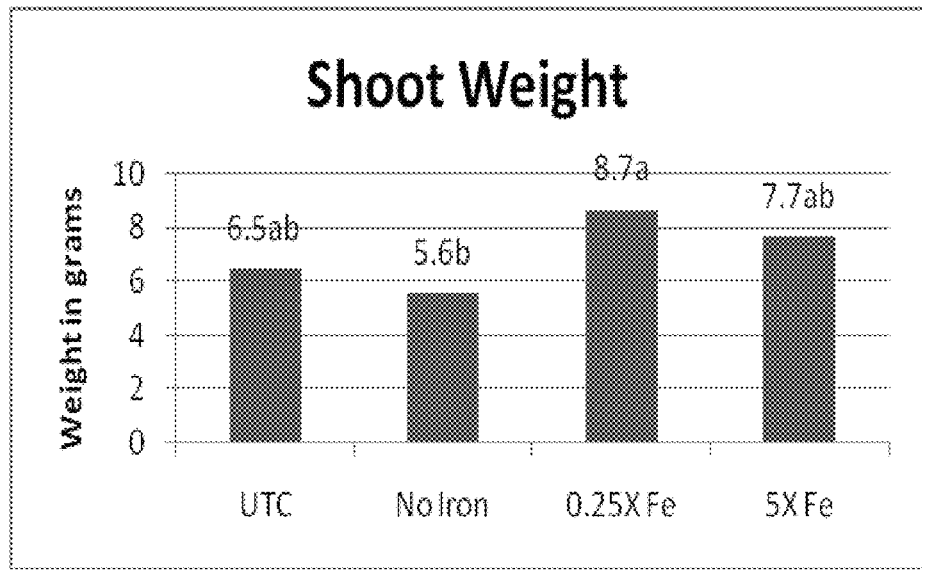

With reference to FIG. 3, plant vigor results are shown for the data obtained from Experiment 1, with the vertical vigor scale representing 5 as best, and 1 as dead. Likewise, FIG. 4 provides the number of leaves per plant, FIG. 5 represents total plant weight, FIG. 6 represents plant root weight, and FIG. 7 represents plant shoot weight. For FIGS. 3-7, the numbers presented above each bar are means. The data in FIGS. 3-7 shows the presence or absence of iron in CPPA has an effect on plant biology. CPPA typically contains from 0.10 to 0.28 grams of Fe for every gram of total organic carbon (TOC), with an average around 0.21, represented by about 0.25 wt. % of the TOC, which is essentially that of the 0.25× Fe sample. As can be seen from the results shown in FIGS. 3-7, CPPA with the average amount of iron naturally present provides a positive biological effect on plants after treatment. The data indicates an excess of iron (5× Fe) provides a generally poorer biological effect relative to the normal iron amount, but yet superior to the No Iron sample. As further shown in the data of FIGS. 3-7, the No Iron treatment provided a biological effect less than the UTC, which can be described as a biological inhibition or toxicity. From this data, it is clear that iron in combination with CPPA affects the biological activity of plants, at least with regard to vigor, the number of leaves per plant, total plant weight, root, and shoot weights, any of which are direct or indirect indicators of one or more biological processes of plants. Such effect of Fe in combination with CPPA provides optimum efficacy when the weight of the iron is approximately 10%, 15%, 20%, 25%, 30%, 35%, 40%, 45% or less than 50% of the weight of the organic carbon in the CPPA.

Experiment Fe-1A: The data reported above for Experiment 1 was for the treatments applied at the equivalent of 520 mg TOC/ha. This is a typical foliar application rate for a CPPA product. Thus, three other rates were evaluated in this experiment, namely 260 mg TOC/ha, 1040 mg TOC/ha and 2080 mg TOC/ha rates. The samples were the same as used above. FIGS. 8A-8D depict data results for these compositions, where the y axis is average weight in grams for the plant, root, and shoot weight.

From the data in FIGS. 8A-8D, the sample without Fe is basically equivalent to the UTC. Adding iron at 25 wt % of the TOC yields a significant improvement in plant biologic function which is manifested in an increase in plant weight, root weight and shoot weight, regardless of the application rate used. However, the improvement appears to plateau at the 260 mg/ha rate with a slight decrease as the application rate of iron increases. It is also observed that for the 260 and 520 mg TOC/ha rates treatment with the high iron concentration actually reduces the biological response compared to the low Fe concentration. For the two highest rates of TOC, the responses appear to be optimal for higher amount of iron than compared to lower iron amounts.

Figure 8A:
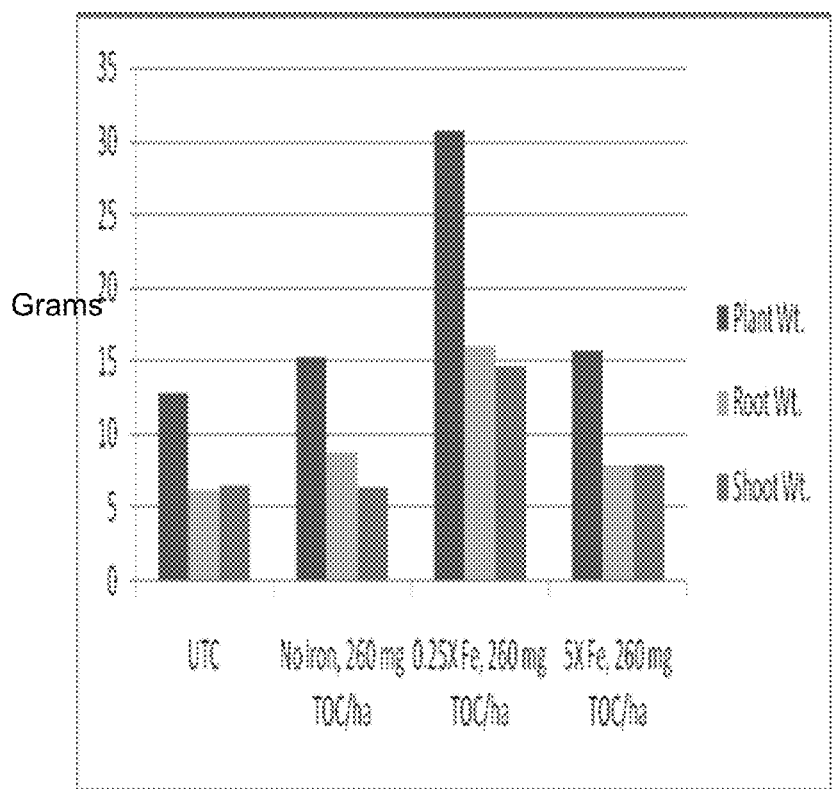
FIGS. 8A-8G. Graphical representations of biological response observed for plant weight, plant root weight, and plant shoot weight for exemplary compositions of the present disclosure comprising combinations of iron and Total Organic Carbon (w/w %)
Figure 8B:
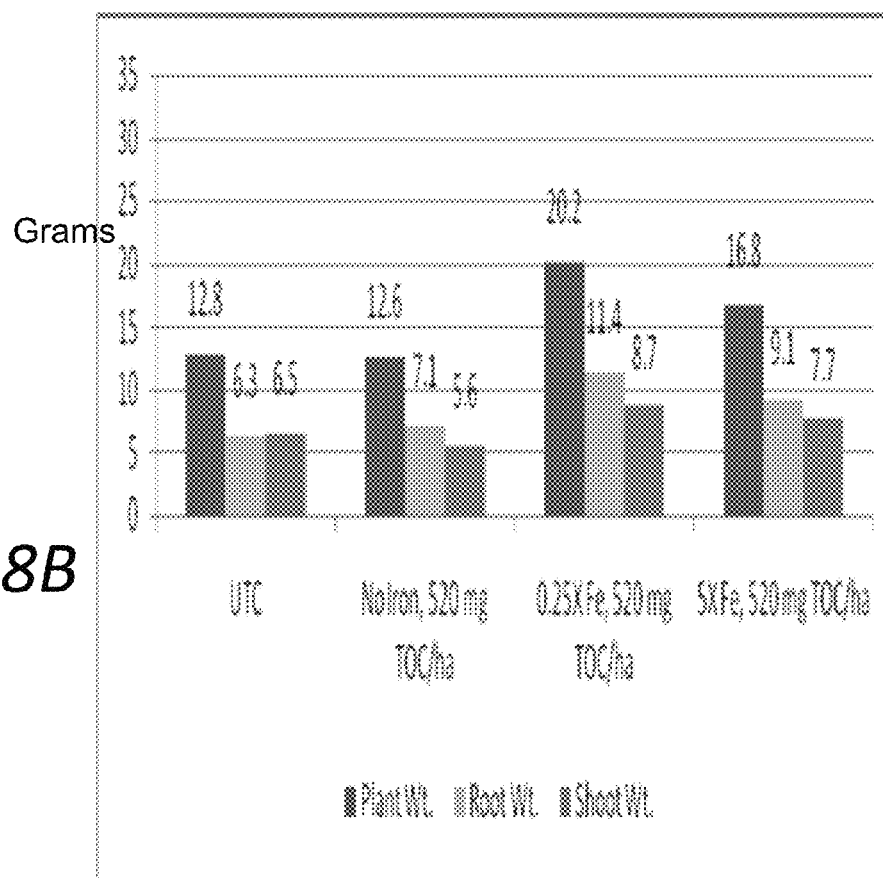
Figure 8C:
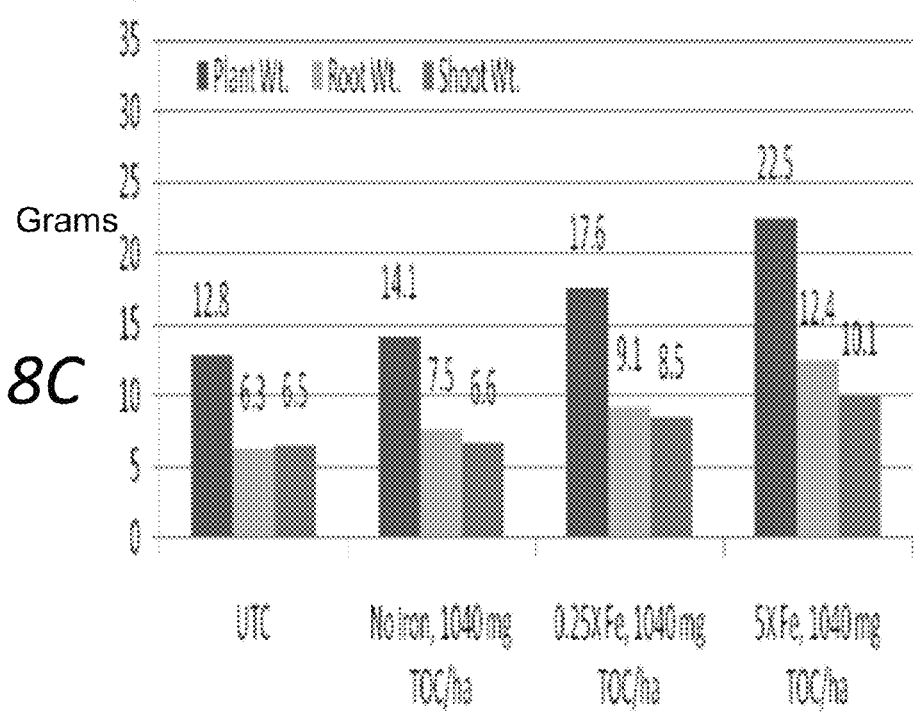
Figure 8D:
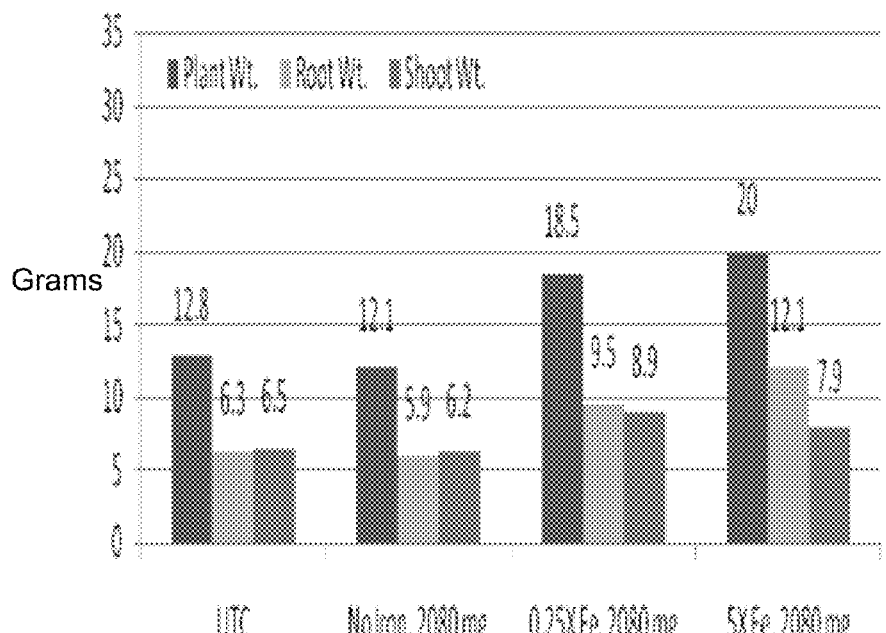
Figure 8E:
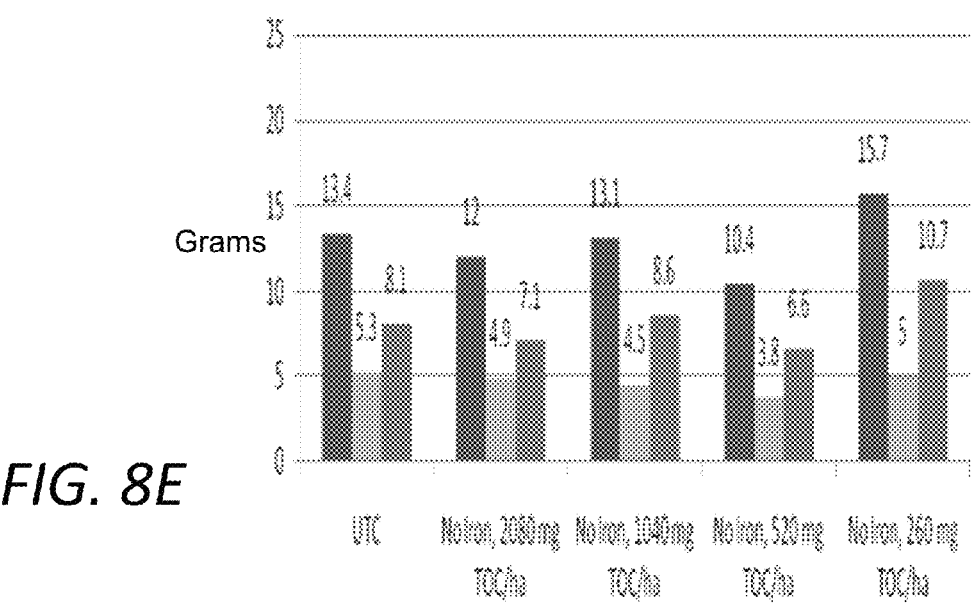
Figure 8F:
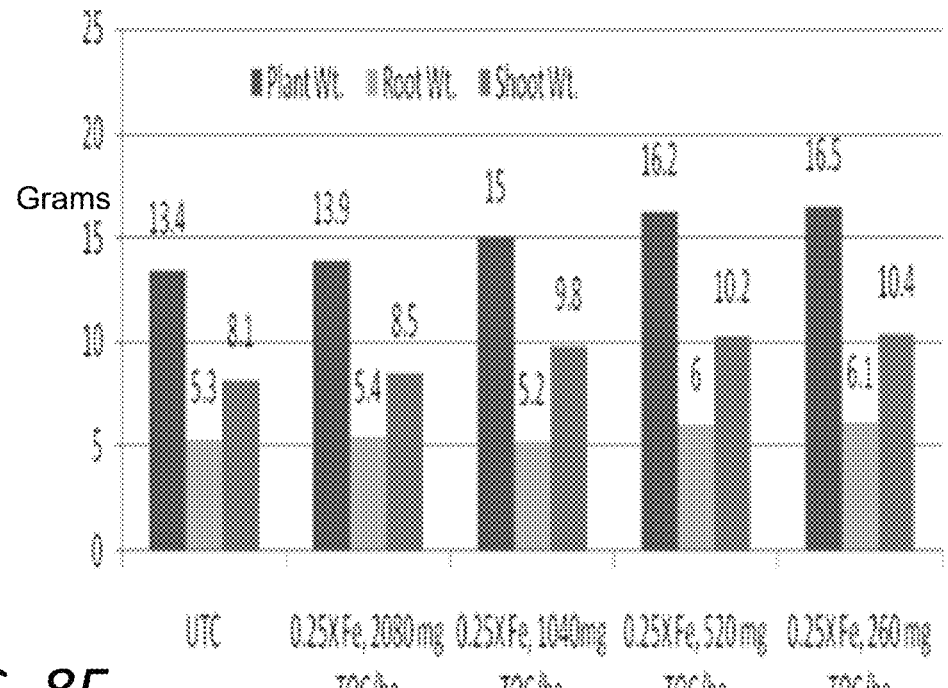
Figure 8G:
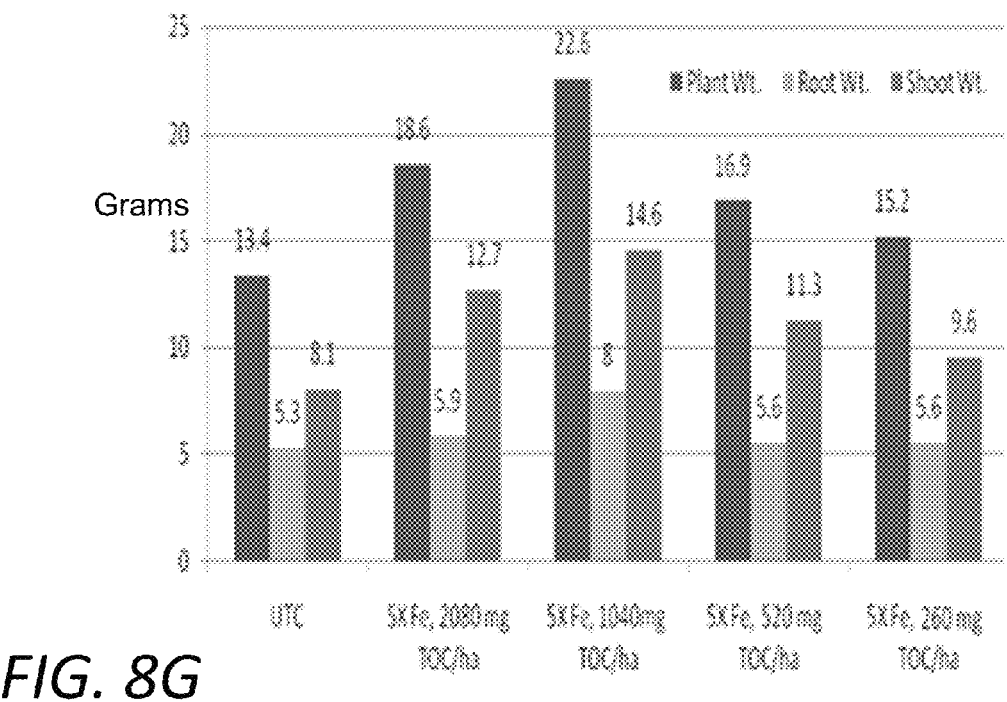

Experiment Fe-1B: A second set of pots were, identical to the set of Experiment Fe-1A, received the same treatments as in the previous discussion, but instead of being assessed after 14 days, they received a second application which was identical to the first for each pot. Then after 14 days, these plants were assessed in the same way as the first assessment. FIGS. 8E-8G plant weight results are plotted for each of the 4 CPPA rates without iron, the 0.25× Fe sample, and the 5× Fe sample. FIG. 8E indicates that for the "No Iron" CPPA sample there is very little in the way of rate response, and none of the differences are statistically significant. FIG. 8F indicates that for the 0.25× Fe CPPA sample, the responses are greatest at the lowest rate and decrease as the rate increases. FIG. 8G indicates that for the 5× Fe CPPA sample, the response is greater at the two highest rates and decreases as the rate decreases. These results show that the amount of iron in combination with CPPA has a direct impact on plant biological response. In one aspect, the data demonstrates that as the amount of iron increases, the amount of CPPA should be increased to achieve the optimum biological effect on the plant.

Experiment Fe-2: Foliar Spray of CPPA/Fe Compositions—The purpose of this experiment was to evaluate the biological effect (e.g., growth and development) of plants when treated with samples from different batches of CPPA, each with a different amount of naturally occurring iron. Weight percent iron in these samples ranged from about 10% to about 30% (w/w) of the weight of organic carbon in CPPA. Tomatoes (*Lycopersicon* es.) were produced from seed and transplanted into 3 inch by 3 inch pots for this experiment. There were 11 treatments plus an untreated check with 10 replicates per treatment arranged in a Randomized Complete Block design. All pots received an application of CPPA as a foliar spray 19 days after transplanting. Pots were treated with CPPA at a rate equivalent to 520 mg of organic carbon per hectare, and with UTC. Thirteen days after foliar application, the plants were measured for root weights.

Figure 9A:
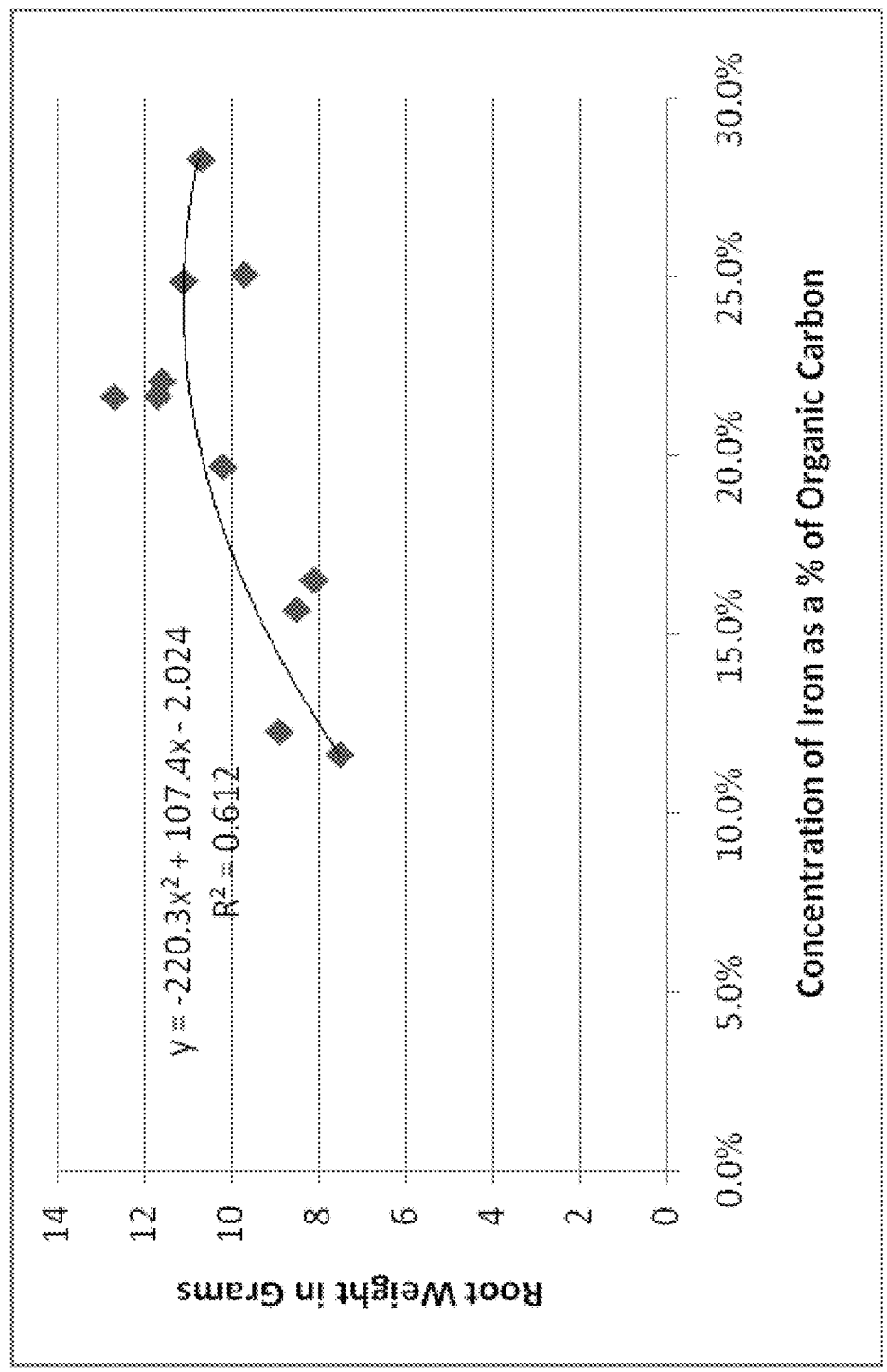
FIG. 9A-9B. Regression curves of plant root weight verses Fe/Total Organic Carbon (w/w %) for exemplary compositions of the present disclosure.

A regression curve is shown in FIG. 9A, showing root weight of plants treated with CPPA containing varying amounts of Fe. Regression of the root weight verses the percentage of Fe to the organic carbon for each CPPA sample (w/w %) was best fit to a second degree polynomial with a maximum at around 23% iron to organic carbon. Other compositional characteristics were evaluated in a similar manner, but none of them correlated with the measured root weights. Other biological indicators were measured and evaluated versus the iron content, however, the correlation was not statistically significant.

Figure 9B:
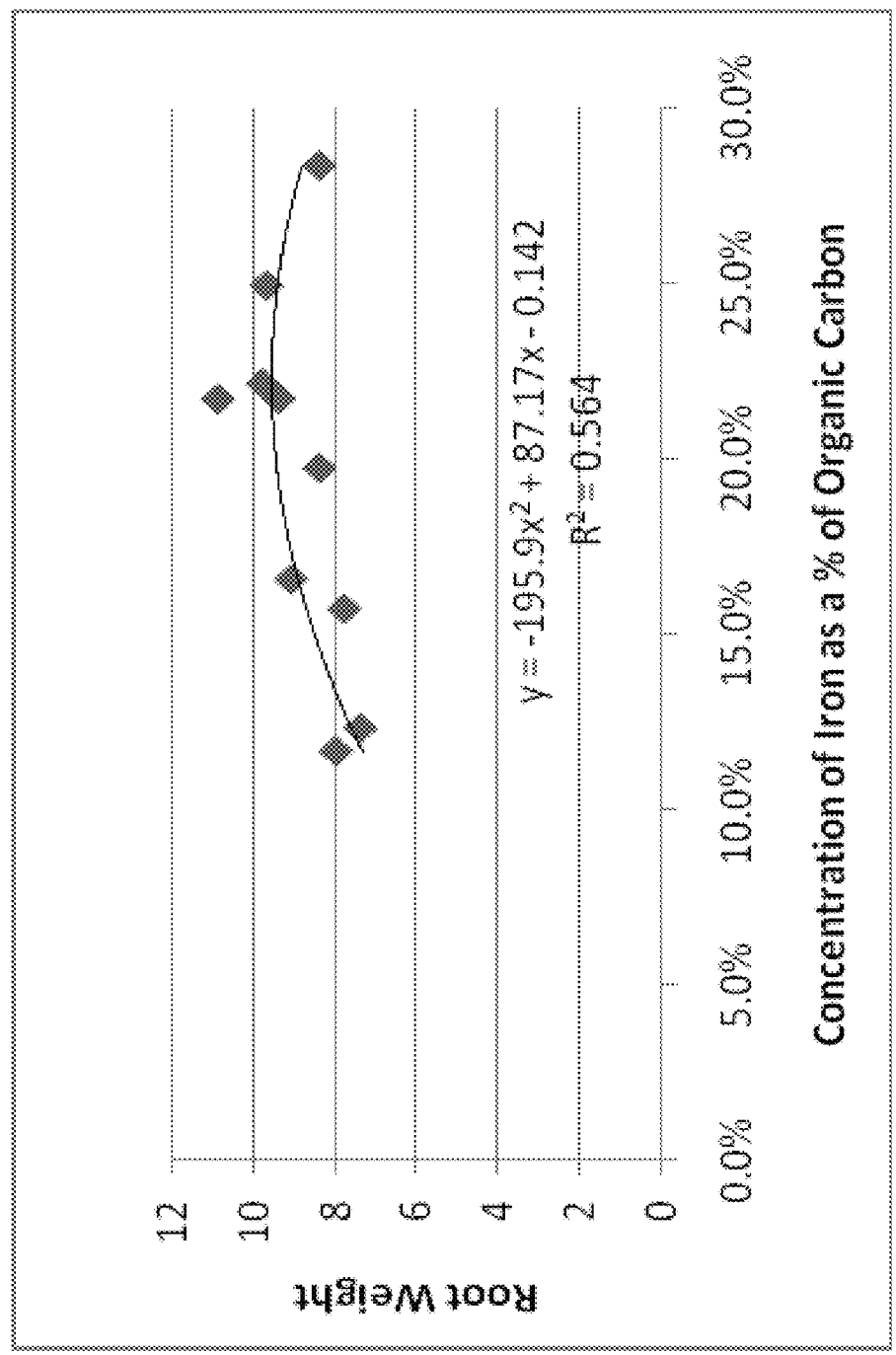

Experiment Fe-3: Multiple and/or Sequential Treatments with CPPA/Fe Compositions—The purpose of this experiment was to determine whether plants treated with more than one application of the CPPA/Fe formulations of Experiment Fe-2 would show equivalent or improved biological effect (e.g., growth and development) compared to a single treatment. Samples (CPPA with and without Fe) and UTC were as described in Fe-1. All pots received an application of CPPA as a foliar spray 19 days after transplanting. The untreated check was treated with only water, and the other pots were treated with CPPA at a rate equivalent to 520 mg of organic carbon per hectare. Iron in these samples ranged from about 10% of the carbon in CPPA by weight to about 30% (w/w). Thirteen days after the initial application, the plants were treated a second time with the same CPPA sample they were treated with initially. Fourteen days after the second treatment, all plants were harvested and root weights were measured. In this experiment, the root weights for each plant measured 14 days after the second foliar application of CPPA were plotted on the y axis of a scatter diagram and the iron as a percentage of the organic carbon for each CPPA sample was plotted on the x axis and a trend line was determined. Results are shown in FIG. 9B, which depicts root weight of plants treated twice with CPPA samples containing varying amounts of Fe versus the amount of Fe in each sample. As in the previous experiment, the best fit regression was a second degree polynomial with a maximum at around 22% iron to carbon. Other compositional characteristics were evaluated in a similar manner, with insignificant correlation with the measured weights. Also, other growth factors were measured and evaluated versus the iron content and again there was no correlation. Both Experiment Fe-2 and Experiment Fe-3 show a clear correlation between the presence of Fe and amount of Fe in combination with CPPA in foliar applications of CPPA and the resultant root growth (biological effect) measured 14 days after the last application.

Figure 9C:
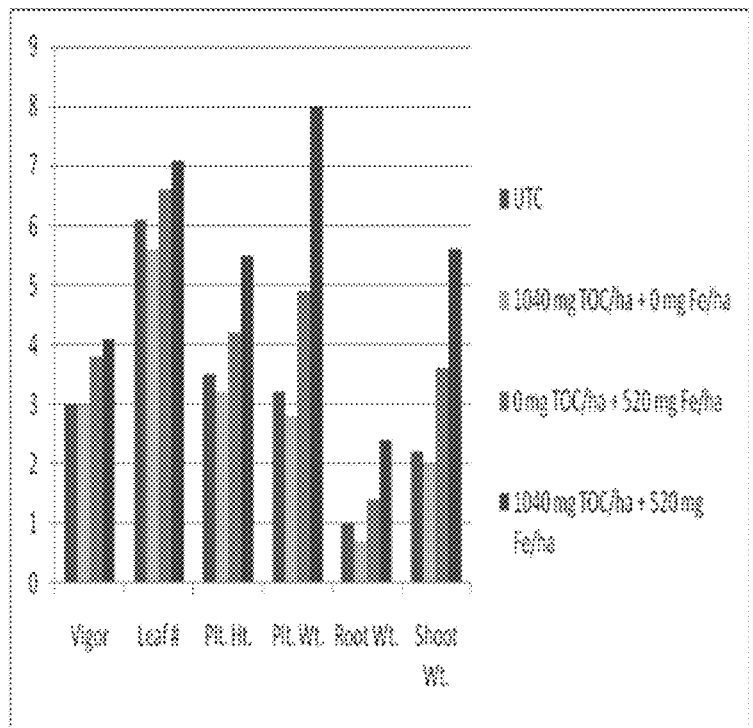
FIGS. 9C-9I. Graphical representations of biological response observed for plant weight, plant root weight, and plant shoot weight for exemplary compositions of the present disclosure comprising combinations of iron and Total Organic Carbon (w/w %)

Experiment Fe-4: The purpose of this experiment was to determine if the addition of low levels of iron to a CPPA sample containing lower than typical amounts of iron (e.g., Fe/TOC=0.135) would increase the biological response of plants. Nominal Fe/TOC ratios for CPPA range from 0.10 to 0.28 but the optimum ratio for "as-is" samples of CPPA, as determined in the previous experiments, is between 0.2 and 0.25. Thus, for this experiment, non-agrochemically effective amounts of iron were combined with CPPA samples. Tomato plants (*Lycopersicon* es.) were produced from seed and transplanted into 3 inch by 3 inch pots. There were 16 treatments plus an untreated check with 20 replicates per treatment arranged in a Randomized Complete Block design. Pots were treated with water (UTC), or CPPA only (3 different rates), Fe only (3 different rates), or CPPA and Fe at each of the rates. The CPPA rates corresponded to 260, 520, and 1040 mg organic carbon (TOC) per hectare and the Fe rates corresponded to 130, 260, and 520 mg Fe per hectare. All pots were treated by foliar application immediately after transplanting. Ten days after the application, ten of the plants were harvested and assessed for vigor, leaf number, plant height, plant weight, root weight, and shoot weight. Results for these assessments with the high rates of CPPA and Fe are shown in FIG. 9C and summarized in Table 1.

TABLE 1

Results for the high rate of CPPA (1040 mg TOC/ha) and the high rate of iron (520 mg Fe/ha) at the First Assessment, 10 days after Application.

| Treatment | mg Fe/ha from CP | mg Fe/ha from FeSO4 | Fe/TOC | Vigor | Leaf # | Plt. Ht. | Plt. Wt. | Root Wt. | Shoot Wt. |
|---|---|---|---|---|---|---|---|---|---|
| UTC | 0 | 0 | | 3.0 c | 6.1 bc | 3.5 c | 3.2 c | 1.0 cd | 2.2 c |
| 1040 mg TOC/ha + 0 mg Fe/ha | 140 | 0 | 0.135 | 3.0 c | 5.6 c | 3.2 cd | 2.8 cd | 0.7 de | 2.0 cd |
| 0 mg TOC/ha + 520 mg Fe/ha | 0 | 520 | | 3.8 b | 6.6 ab | 4.2 b | 4.9 b | 1.4 bc | 3.6 b |
| 1040 mg TOC/ha + 520 mg Fe/ha | 140 | 520 | 0.635 | 4.1 a | 7.1 a | 5.5 a | 8.0 a | 2.4 a | 5.6 a |

Figure 9D:
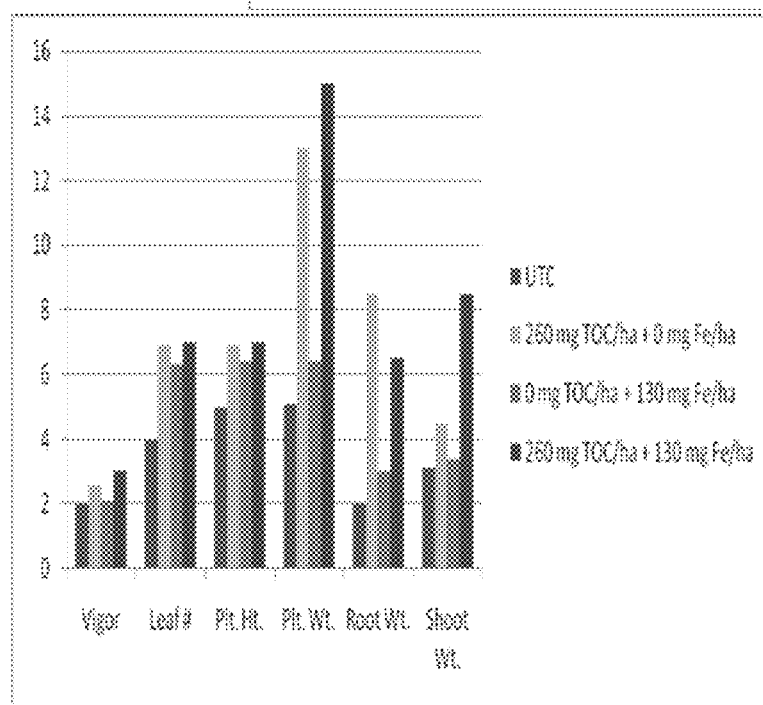

As demonstrated in FIG. 9C and Table 1, the combination of tested non-agriculturally effective Fe concentrations with the tested CPPA concentrations provided a synergistic effect when compared to formulations with just CPPA or just Fe. Additional application rates of CPPA and Fe were evaluated with similar synergistic results observed for the combination of CPPA with amounts of iron. Twenty days after transplanting, the remaining ten plants in each treatment were assessed. Results for three of the treatments are shown in Tables 2, 3, and 4 and FIGS. 9D, 9E, and 9F. As shown in the data, for the combination of low application rates of CPPA in combination with low, non-agriculturally effective application rates of Fe, a significant, synergistic improved biological response (e.g. plant weight, root weight, and shoot weight) was observed compared with either CPPA alone or Fe alone.

Figure 9E:
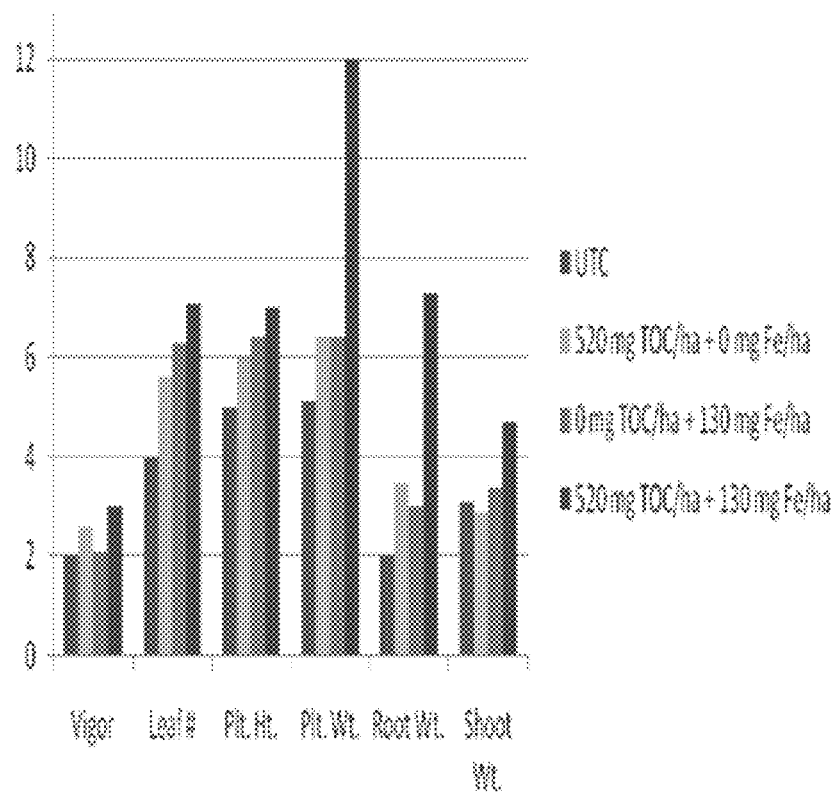

Likewise, as shown in Table 3 and FIG. 9E, intermediate application rates of CPPA (520 mg TOC/ha) in combination with low, non-agriculturally effective application rates of Fe showed synergistic effects compared to either CPPA or Fe alone. For the combination of the intermediate application rate of CPPA in combination with low, non-agriculturally effective application rate of Fe resulted in nearly a 100% increase in total plant weight versus either treatment alone, e.g., root weight was increased by more than 100% versus either treatment alone.

Figure 9F:
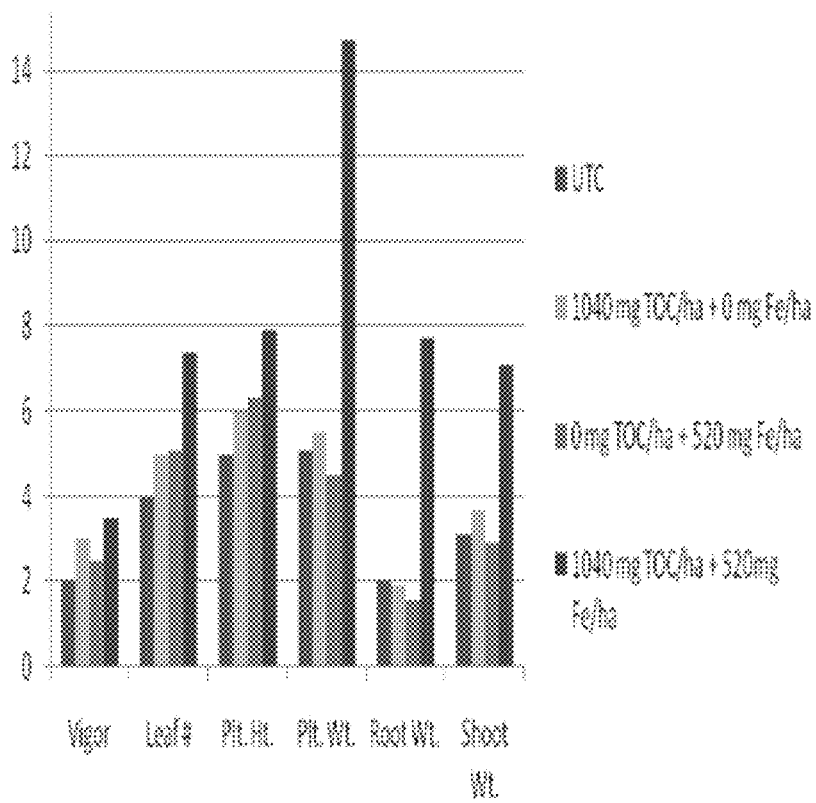

High application rates of CPPA and a high, non-agriculturally effective application rate of Fe were evaluated with results shown in FIG. 9F and Table 4. The high, non-agriculturally effective application rate of Fe treatment alone had an apparent slightly negative biological effect on the plant, root and shoot weights, although it was not statistically significant. The high application rate of the CPPA alone was equivalent to the UTC. However, the combination of a high application rate CPPA and a high, non-agriculturally effective application rate of Fe produced results more than 2× better than either treatment alone.

Figure 9G:
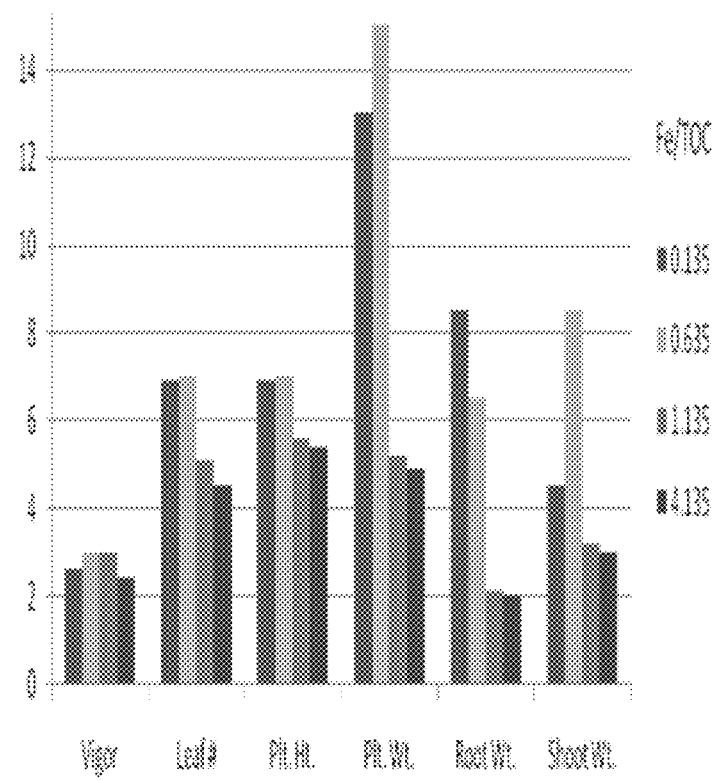

It was also observed that for the low CPPA application rate, the apparent synergistic biological response from the added iron was at the low, non-agriculturally effective amount iron. As iron increased, the growth responses decreased. These results are shown in Table 5 and FIG. 9G where the amount of Fe to the TOC (of CPPA) is expressed as a ratio. In this case, the ratio of Fe to TOC was determined based on the measured Fe content present in the CPPA and the added Fe provided from, e.g., a $FeSO_4$ solution.

Figure 9H:
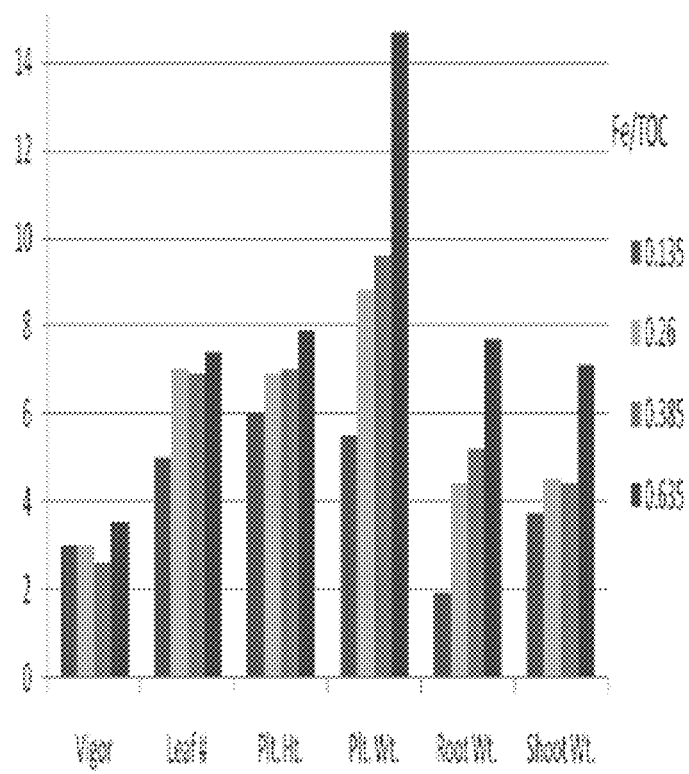

In contrast to that described immediately above, at the high rate of CPPA, a completely opposite effect was observed as seen in Table 6 and FIG. 9H. In this case, the biological response to the high level of CPPA increased as the rate of the Fe increased with the highest rate of Fe yielding the greatest biological response. From these two examples, it appears that the optimum rate for plant response when a non-agriculturally effective amount of Fe is added to CPPA occurs at a ratio of Fe to TOC around 0.63. As the amount of Fe increases, it is observed that an increase in the TOC rate will maintain the optimum ratio between Fe and TOC.

TABLE 2

Results for the low rate CPPA (260 mg TOC/ha) and low rate Fe (130 mg Fe/ha) at the second assessment 20 days after application. Means followed by same letter do not significantly differ (P = 0.05, Duncan's New MRT)

| Treatment | mg Fe/ha from CP | mg Fe/ha from FeSO4 | Fe/TOC | Vigor | Leaf # | Plt. Ht. | Plt. Wt. | Root Wt. | Shoot Wt. |
|---|---|---|---|---|---|---|---|---|---|
| UTC | 0 | 0 | | 2.0 c | 4.0 c | 5.0 d | 5.1 c | 2.0 cd | 3.1 d |
| 260 mg TOC/ha + 0 mg Fe/ha | 35 | 0 | 0.135 | 2.6 ab | 6.9 a | 6.9 ab | 13.0 ab | 8.5 a | 4.5 bc |
| 0 mg TOC/ha + 130 mg Fe/ha | 0 | 130 | | 2.1 c | 6.3 ab | 6.4 abc | 6.4 c | 3.0 c | 3.4 cd |
| 260 mg TOC/ha + 130 mg Fe/ha | 35 | 130 | 0.635 | 3.0 a | 7.0 a | 7.0 a | 15.0 a | 6.5 b | 8.5 a |

TABLE 3

Combination of middle rate of CPPA (520 mg TOC/ha) and low rate of Fe (130 mg Fe/ha) at the first assessment, 20 days after application. Means followed by same letter do not significantly differ (P = 0.05, Duncan's New MRT)

| Treatment | mg Fe/ha from CP | mg Fe/ha from FeSO4 | Fe/TOC | Vigor | Leaf # | Plt. Ht. | Plt. Wt. | Root Wt. | Shoot Wt. |
|---|---|---|---|---|---|---|---|---|---|
| UTC | 0 | 0 | | 2.0 c | 4.0 d | 5.0 d | 5.1 b | 2.0 bcd | 3.1 ab |
| 520 mg TOC/ha + 0 mg Fe/ha | 70 | 0 | 0.135 | 2.6 ab | 5.6 bc | 6.0 bc | 6.4 b | 3.5 bc | 2.9 bc |
| 0 mg TOC/ha + 130 mg Fe/ha | 0 | 130 | | 2.1 c | 6.3 ab | 6.4 ab | 6.4 b | 3.0 b | 3.4 ab |
| 520 mg TOC/ha + 130 mg Fe/ha | 70 | 130 | 0.385 | 3.0 a | 7.1 a | 7.0 a | 12.0 a | 7.3 a | 4.7 a |

TABLE 4

The combination of the high rate of CPPA (1040 mg TOC/ha) and high rate of Fe( 520 mg Fe/ha) at the second assessment, 20 days after application. Means followed by same letter do not significantly differ (P = 0.05, Duncan's New MRT)

| Treatment | mg Fe/ha from CP | mg Fe/ha from FeSO4 | Fe/TOC | Vigor | Leaf # | Plt. Ht. | Plt. Wt. | Root Wt. | Shoot Wt. |
|---|---|---|---|---|---|---|---|---|---|
| UTC | 0 | 0 | | 2.0 d | 4.0 c | 5.0 d | 5.1 b | 2.0 b | 3.1 bcd |
| 1040 mg TOC/ha + 0 mg Fe/ha | 140 | 0 | 0.135 | 3.0 b | 5.0 b | 6.0 bc | 5.5 b | 1.9 b | 3.7 bc |
| 0 mg TOC/ha + 520 mg Fe/ha | 0 | 520 | | 2.5 c | 5.1 b | 6.3 b | 4.5 b | 1.6 bc | 2.9 cd |
| 1040 mg TOC/ha + 520 mg Fe/ha | 140 | 520 | 0.635 | 3.5 a | 7.4 a | 7.9 a | 14.7 a | 7.7 a | 7.1 a |

TABLE 5

Effect of increasing Fe in the 260 mg TOC/ha treatment

| Treatment | Fe/TOC | Total Fe (mg/ha) | Vigor | Leaf # | Plt. Ht. | Plt. Wt. | Root Wt. | Shoot Wt. |
|---|---|---|---|---|---|---|---|---|
| 260 mg TOC/ha + 0 mg/ha Fe from FeSO4 | 0.135 | 35.1 | 2.6 | 6.9 | 6.9 | 13 | 8.5 | 4.5 |
| 260 mg TOC/ha + 130 mg Fe/ha from FeSO4 | 0.635 | 165.1 | 3 | 7 | 7 | 15 | 6.5 | 8.5 |
| 260 mg TOC/ha + 260 mg Fe/ha from FeSO4 | 1.135 | 295.1 | 3 | 5.1 | 5.6 | 5.2 | 2.1 | 3.2 |
| 260 mg TOC/ha + 520 mg Fe/ha from FeSO4 | 4.135 | 555.1 | 2.4 | 4.5 | 5.4 | 4.9 | 2 | 3 |

TABLE 6

Effect of increasing Fe in the 1040 mg TOC/ha CPPA treatments

| Treatments | Fe/TOC | Total Fe (mg/ha) | Vigor | Leaf # | Plt. Ht. | Plt. Wt. | Root Wt. | Shoot Wt. |
|---|---|---|---|---|---|---|---|---|
| 1040 mg TOC/ha + 0 mg Fe/ha from FeSO4 | 0.135 | 140.4 | 3 | 5 | 6 | 5.5 | 1.9 | 3.7 |
| 1040 mg TOC/ha + 130 mg Fe/ha from FeSO4 | 0.26 | 270.4 | 3 | 7 | 6.9 | 8.8 | 4.4 | 4.5 |
| 1040 mg TOC/ha + 260 mg Fe/ha from FeSO4 | 0.385 | 400.4 | 2.6 | 6.9 | 7 | 9.6 | 5.2 | 4.4 |
| 1040 mg TOC/ha + 520 mg Fe/ha from FeSO4 | 0.635 | 660.4 | 3.5 | 7.4 | 7.9 | 14.7 | 7.7 | 7.1 |

Figure 9I:
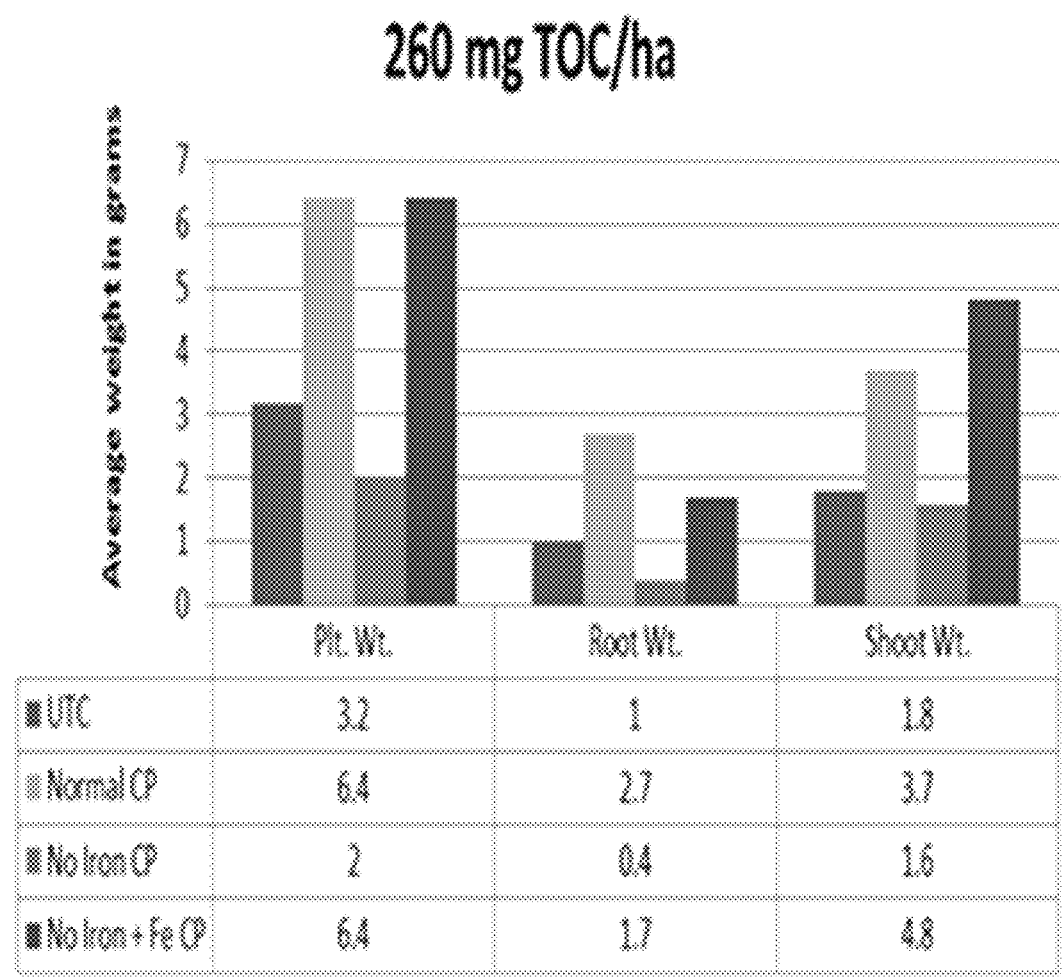
Figure 10:
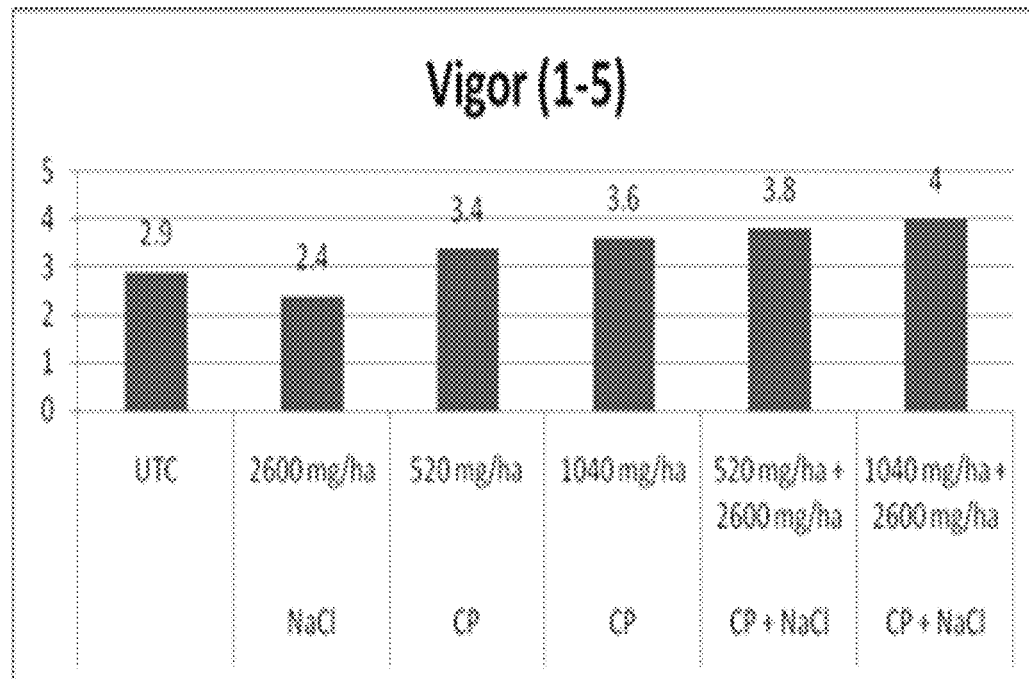
FIG. 10. Graphical representation of plant vigor verses control after treatment with embodiments of the present disclosure.
Figure 11:
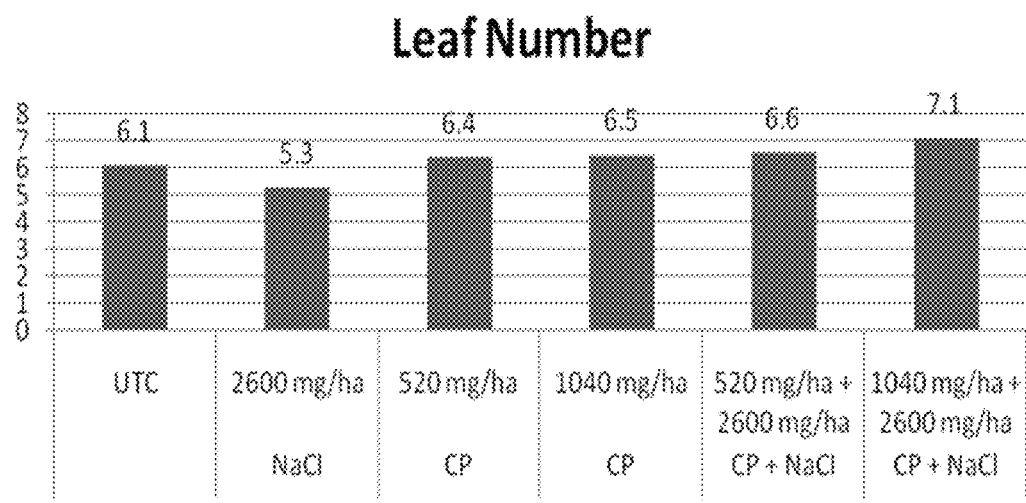
FIG. 11 Graphical representation of leaves per plant verses control after treatment with embodiments of the present disclosure.
Figure 12:
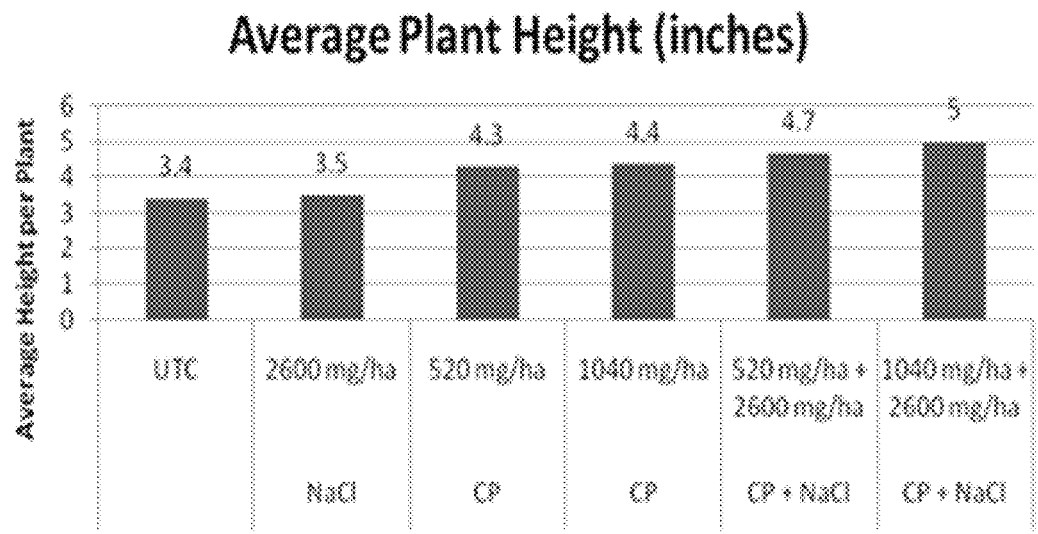
FIG. 12. Graphical representation of average plant height verses control after treatment with embodiments of the present disclosure.
Figure 13:
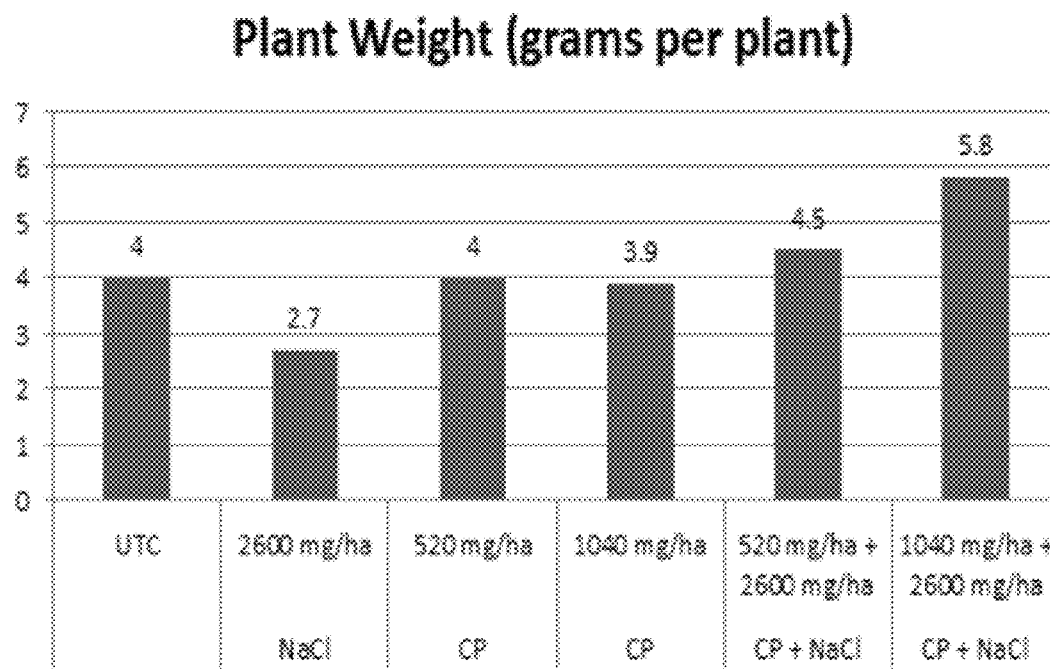
FIG. 13. Graphical representation of plant weight verses control after treatment with embodiments of the present disclosure.
Figure 14:
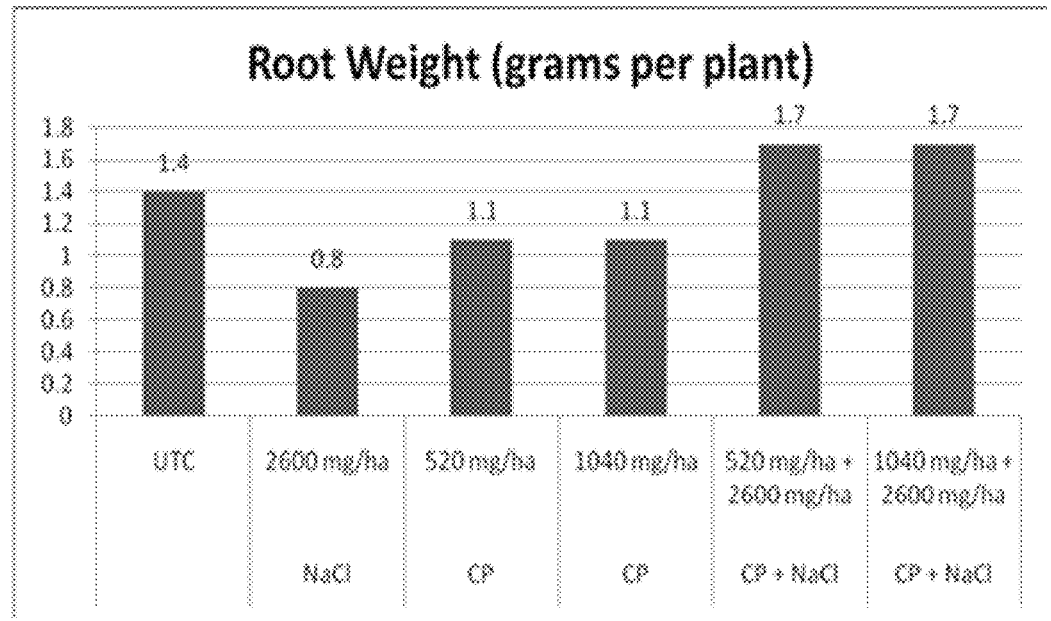
FIG. 14. Graphical representation of plant root weight verses control after treatment with embodiments of the present disclosure.
Figure 15:
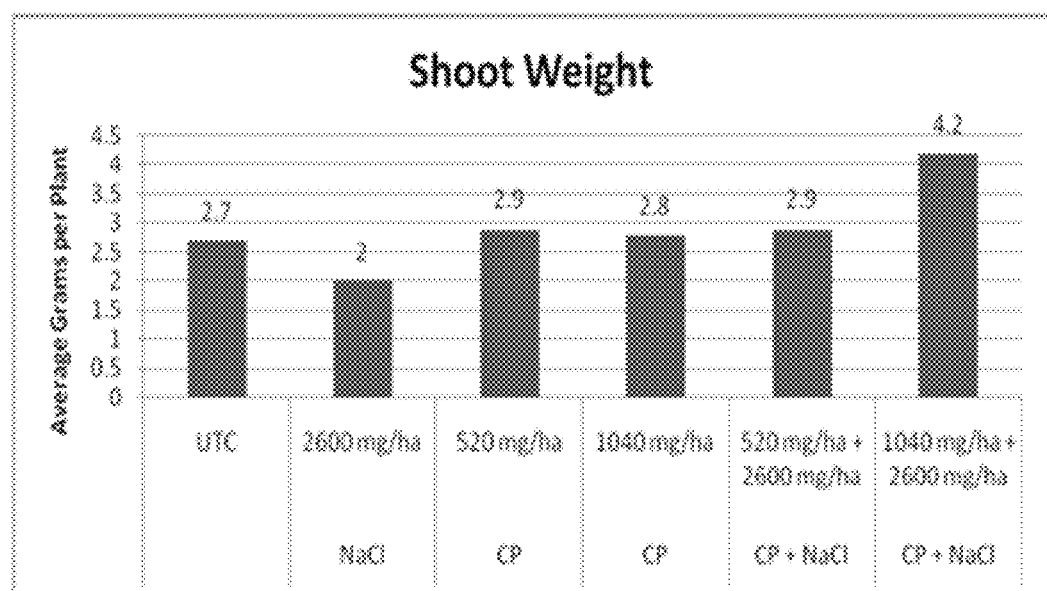
FIG. 15. Graphical representation of plant shoot weight verses control after treatment with embodiments of the present disclosure.
Figure 16:
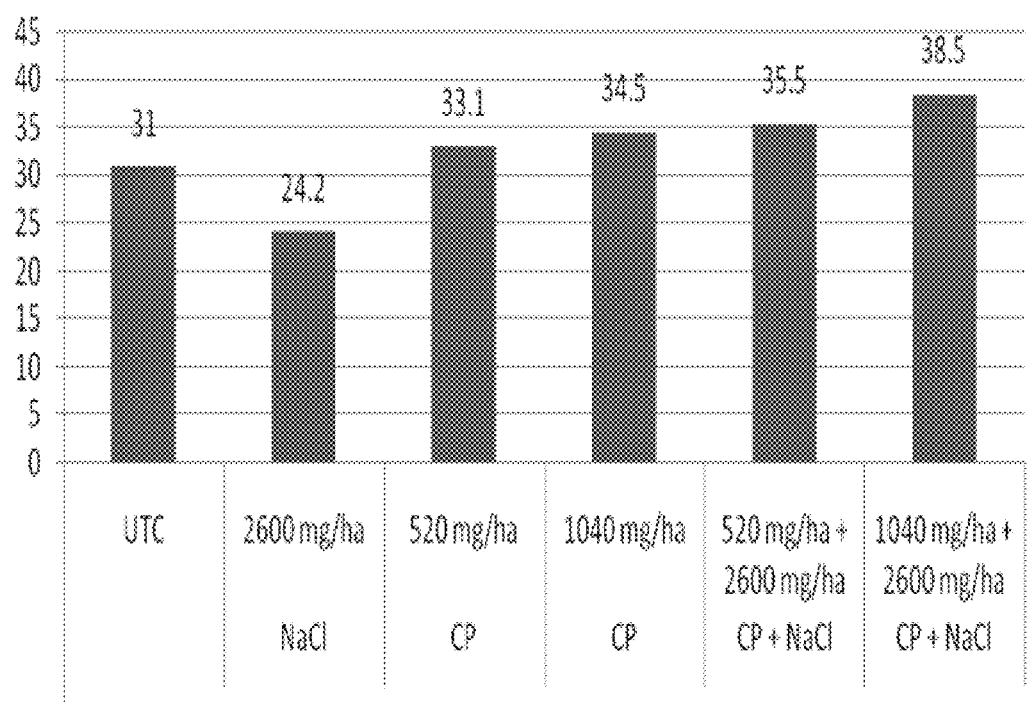
FIG. 16. Graphical representation of plant leaf conductance verses control after treatment with embodiments of the present disclosure.

Experiment 5: Reversibility of Fe concentration in CPPA Formulations. The purpose of this experiment was to determine the effect on plant biology after removing Fe from CPPA and then adding back Fe to the CPPA to the original level. For this experiment, tomato plants (*Lycopersicon* es.) were produced from seed and transplanted into 3 inch by 3 inch pots. There were 3 treatments plus an untreated check with 10 replicates per treatment arranged in a Randomized Complete Block design. All pots received an application of CPPA as a foliar spray at the time they were transplanted. The untreated check was treated with only water, and the other pots were treated with CPPA at a rate equivalent to 260 mg of organic carbon per hectare. Iron in the initial sample (designated "Normal CPPA") was determined to be 13.6% by weight of the organic carbon. The Normal CPPA sample was then treated with a cation exchange resin (AG MP-50 Resin, Bio-Rad Laboratories, 2000 Alfred Nobel Drive, Hercules, Calif. 94547) to remove the iron (designated "No Iron CPPA"). Iron, as iron sulfate, was added to the No Iron CPPA sample so the iron content was equivalent to about 13.6% of the organic carbon (designated "No Iron+Fe CPPA"). Ten days after the application, all plants were harvested and the plants were assessed for plant weight, root weight, and shoot weight. Results are shown in FIG. 9I, and show that the "Normal CPPA" treatment at 260 mg TOC/ha promoted a significant biological response in the plant as measured by plant, root, and shoot weights. At the same application rate, the No Iron CPPA sample inhibited biological responses as indicated by lower weights compared to the untreated check. However, when the iron was added back in, as in the No Iron+Fe CPPA sample, biological responses were returned to the same level they were with the Normal sample, demonstrating that the effects of removing the iron from the CPPA are reversible at this application rate and likely at other application rates.

These experiments demonstrate the biological effect of Fe in combination with CPPA as a foliar treatment. Soil and/or locus treatment of CPPA/Fe compositions is believed to provide similar results. Other transition metal ions, alone or in combination with iron, such as ions of manganese (Mn), zinc (Zn), and/or copper (Cu), are expected to display similar biological effects when combined with CPPA as a foliar and/or soil or locus treatment.

Alkali (Earth) Metal Salt in Combination with CPPA

The purpose of these experiments were to: (1) determine if a foliar application to of CPPA in combination with phytotoxic levels of alkali (earth) salts would mitigate the phytotoxicity in plants, and if (2) there was a synergistic effect between the CPPA and alkali (earth) salts in positively effecting biological activity of plants.

Experiment Salt-1: CPPA/NaCl Composition—Foliar Application—For this experiment, tomato plants (*Lycopersicon* es.) were produced from seed and transplanted into 3 inch by 3 inch pots. There were a total of 5 treatments plus an untreated check, each with 10 replicates per treatment arranged in a randomized block design. Aqueous solutions of CPPA (1000 mg TOC/L) and NaCl (5000 mg/L, hereinafter "salt") were used for this experiment and all plants were treated with a foliar application at the time they were transplanted into the pots. Each treatment comprised samples treated with CPPA alone, salt alone, or CPPA plus salt. Two rates of CPPA were used; the first was equivalent to 520 mg of TOC per hectare and a second equivalent to 1040 mg of TOC per hectare. Salt was applied at a rate equivalent to 2.6 g of salt per hectare. All treatments were diluted with water to provide a final spray volume equivalent to 208 lit per hectare, made with a spray bottle, with just enough spray solution to wet the leaf surface of each plant. Treatments for Experiment Salt-1 are summarized in Table 7.

TABLE 7

Treatments, compositions, application rate for Experiment Salt-1

| Treatment | | Rate (mg/ha) |
|---|---|---|
| 1 | UTC | |
| 2 | CPPA (1000 mg/L TOC) | 520 |
| 3 | CPPA (1000 mg/L TOC) | 1040 |
| 4 | NaCl (5000 mg/L) | 2600 |
| 5 | CPPA (1000 mg/L TOC) | 520 |
|   | NaCl (5000 mg/L) | 2600 |
| 6 | CPPA (1000 mg/L TOC) | 1040 |
|   | NaCl (5000 mg/L) | 2600 |

Ten days after treatment the plants were assessed for vigor, leaf number, plant height, plant weight, root weight, shoot weight, and leaf conductance using a SPAD meter and are summarized in Table 8 and depicted in FIGS. 10-16.

TABLE 8

Summarized biological effects of compositions of CPPA/salt on tomato plant at 1000 mg/ha CPPA and 0 mg or 5000 mg/ha salt at application rates of 520 mg/ha, 1040 mg/ha, and 2600 mg/ha.

| | Rate (mg/ha) | Vigor | Leaf # | Plt. Ht. | Plt. Wt. | Root Wt. | Shoot Wt. | SPAD |
|---|---|---|---|---|---|---|---|---|
| UTC | | 2.9 b | 6.1 bcd | 3.4 b | 4.0 b | 1.4 ab | 2.7 b | 31 ab |
| CPPA (1000 mg/L TOC) | 520 | 3.4 a | 6.4 abc | 4.3 ab | 4.0 b | 1.1 ab | 2.9 b | 33.1 ab |
| CPPA (1000 mg/L TOC) | 1040 | 3.6 a | 6.5 abc | 4.4 ab | 3.9 b | 1.1 ab | 2.8 b | 34.5 ab |
| NaCl (5000 mg/L) | 2600 | 2.4 b | 5.3 e | 3.5 b | 2.7 c | 0.8 jc | 2.0 c | 24.2 b |
| CPPA (1000 mg/L TOC) NaCl (5000 mg/L) | 520 2600 | 3.8 a | 6.6 ab | 4.7 a | 4.0 b | 1.7 a | 2.9 b | 35.5 a |
| CPPA (1000 mg/L TOC) NaCl (5000 mg/L) | 1040 2600 | 4.0 a | 7.1 a | 5.0 a | 5.8 a | 1.7 a | 4.2 a | 38.5 a |

These results observed and summarized in Table 8 were very consistent, where, in all but one case, the salt treatment alone gave the expected poorest results, indicating a significant amount of phytotoxicity, whereas surprisingly and unexpectedly, in every case where the salt was used in combination with CPPA, complete mitigation of the toxic effects of the salt were observed. Also, in every case, the NaCl plus CPPA treatment, effects of biological activity was observed as good or better than CPPA alone, indicating a significant synergistic effect. For total plant weight and shoot weight, the differences between CPPA alone and the CPPA plus NaCl were statistically significant at $P<0.01$.

Experiment Salt-2: Foliar Treatment of CPPA/salt formulations. The purpose of this experiment was to: (1) determine if a foliar application of low/high application rates of CPPA in combination with phytotoxic levels of salt would mitigate the phytotoxicity of salt exposure in plants, and if (2) there was a synergistic effect between low/high application rates of CPPA and varying salt rate in positively effecting biological activity of plants.

For this experiment, tomato plants (*Lycopersicon* es.) were produced from seed and transplanted into 3 inch by 3 inch pots. There were a total of 8 treatments plus an untreated check, with 20 replicates per treatment arranged in a randomized block design. Aqueous solutions of CPPA (1000 mg TOC/L) and salt (5000 mg/L) were used for this experiment and all plants were treated with a foliar application at the time they were transplanted into the pots. Each treatment contained CPPA alone, salt alone, or CPPA plus salt. Two rates of CPPA were used; the first was equivalent to 260 mg of TOC per hectare and a second equivalent to 1040 mg of TOC per hectare. The NaCl was applied at two rates, equivalent to 1.3 and 2.6 g of NaCl per hectare. All treatments were diluted with water to provide a final spray volume equivalent to 208 lit per hectare, applied with a spray bottle, with just enough spray solution to wet the leaf surface of each plant. Treatments are summarized in Table 9.

TABLE 9

Summary of Treatments for Experiment Salt-2

| TRT. | Formulation | Rate (mg/ha) |
|---|---|---|
| 1 | UTC | |
| 2 | CPPA (1000 mg/L TOC) | 260 |
| 3 | CPPA (1000 mg/L TOC) | 1040 |
| 4 | NaCl (5000 mg/L) | 1300 |
| 5 | NaCl (5000 mg/L) | 2600 |
| 6 | CPPA (1000 mg/L TOC) | 260 |
|   | NaCl (5000 mg/L) | 1300 |
| 7 | CPPA (1000 mg/L TOC) | 260 |
|   | NaCl (5000 mg/L) | 2600 |

TABLE 9-continued

Summary of Treatments for Experiment Salt-2

| TRT. | Formulation | Rate (mg/ha) |
|---|---|---|
| 8 | CPPA (1000 mg/L TOC) | 1040 |
|   | NaCl (5000 mg/L) | 1300 |
| 9 | CPPA (1000 mg/L TOC) | 1040 |
|   | NaCl (5000 mg/L) | 2600 |

Figure 17:
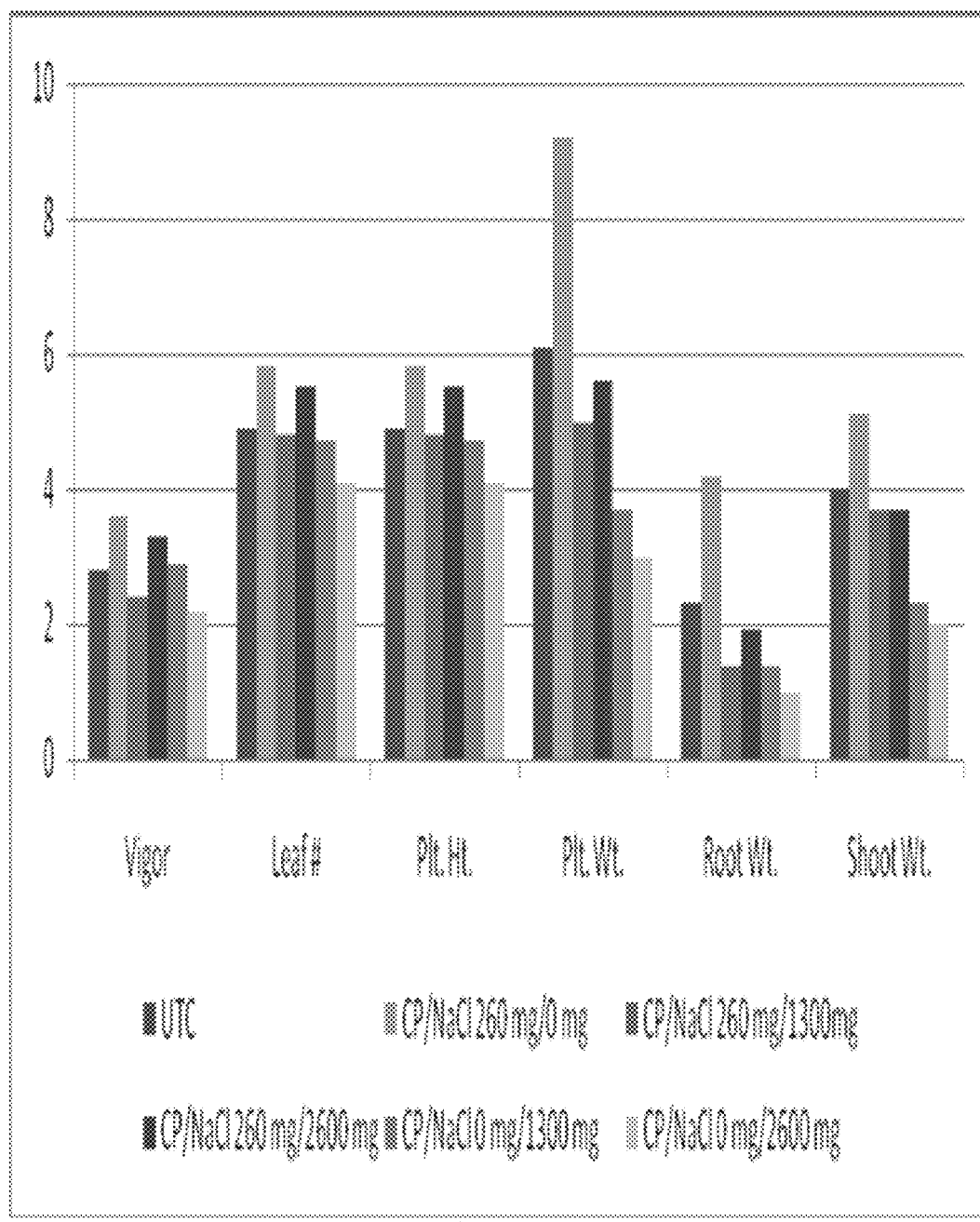
FIG. 17. Graphical representation of plant vigor, leaf number, plant height, plant weight, plant root weight, and plant shoot weight verses control after treatment with embodiments of the present disclosure.

Ten days after applications, ten each of the plant samples in each treatment were assessed for vigor, leaf number, plant height, plant weight, root weight, and shoot weight. Assessments were repeated at twenty days with the remaining ten plants of each treatment and the results were averaged. FIG. 17 depicts observed vigor, leaf number, plant height, plant weight, root weight, and shoot weight results for treatments to the tomato plants with 0 mg and 260 mg CPPA/ha application rate with variable salt application rates, which are also summarized in Table 4.

Figure 18:
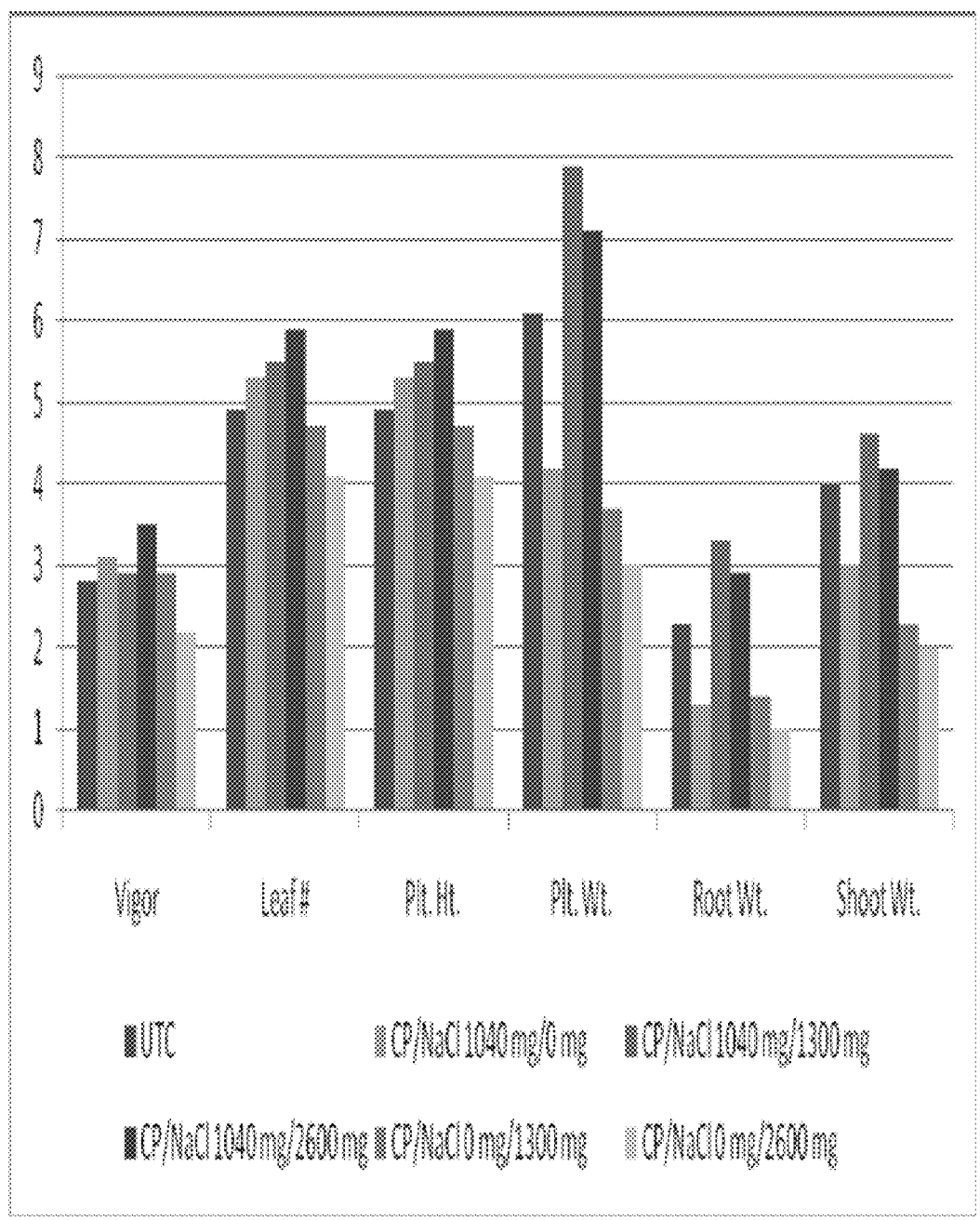
FIG. 18. Graphical representation of plant vigor, leaf number, plant height, plant weight, plant root weight, and plant shoot weight verses control after treatment with embodiments of the present disclosure.

FIG. 18 depicts observed vigor, leaf number, plant height, plant weight, root weight, and shoot weight results for treatments to the tomato plants with 1040 mg CPPA/ha, which is also summarized in Table 10.

TABLE 10

Summarized biological effects of compositions of CPPA/salt on tomato plant with 0 mg CPPA/ha and 1040 mg CPPA/ha, with 1300 mg/salt and 2600 mg/salt

| Treatment | Rate (mg/ha) | Vigor (1-5) | Leaf # | Plt. Ht. (inches) | Plt. Wt. (grams) | Root Wt. (grams) | Shoot Wt. (grams) |
|---|---|---|---|---|---|---|---|
| UTC | | 2.8 ef | 4.9 cd | 4.9 c | 6.1 c | 2.3 b | 4.0 cd |
| CP/NaCl | 1040 mg/0 mg | 3.1 bc | 5.3 bc | 5.3 ab | 4.2 d | 1.3 d | 3.0 e |
| CP/NaCl | 1040 mg/1300 mg | 2.9 cd | 5.5 b | 5.5 ab | 7.9 a | 3.3 a | 4.6 a |
| CP/NaCl | 1040 mg/2600 mg | 3.5 a | 5.9 a | 5.9 a | 7.1 a | 2.9 a | 4.2 bc |
| CP/NaCl | 0 mg/1300 mg | 2.9 de | 4.7 de | 4.7 cd | 3.7 d | 1.4 cd | 2.3 e |
| CP/NaCl | 0 mg/2600 mg | 2.2 g | 4.1 f | 4.1 e | 3 de | 1.0 d | 2.0 ef |

In experiment Salt-2, both rates (260 mg/ha and 1040 mg/ha) of CPPA were shown to mitigate the negative responses (phytotoxicity) caused by the exposure of salt. From the data of FIG. 17, it was observed that at the 260 mg/ha rate of CPPA, the mitigation effect was greater for the higher salt exposure rate (e.g., 2600 mg/ha salt) than for the lower rate (e.g., 1300 mg/ha salt). However at the 260 mg/ha CPPA rate, there was a substantial suppression of a synergistic effect, since in all cases, the CPPA alone prompted a larger positive response in the plants than the same rate of CPPA with either rate of salt. In FIG. 18, which depicts the higher CPPA rate of 1040 mg/ha, not only were the negative salt responses mitigated, but there was observed a synergistic effect between CPPA and the salt. The synergistic effect on plant biology was noted for both the low and high rates of salt, but this synergistic effect was slightly greater for the lower rate of salt.

Experiment Salt-3:

Soil Treatments of CPPA/salt formulations—The purpose of this experiment was to determine if there is a synergistic biological effect on plants when CPPA in combination with salt was applied to soil or locus of a plant at time of planting.

For this experiment, wheat seeds (*Triticum aestivum*) were planted in small pots, approximately 1 inch in diameter and an inch in depth. There were a total of 8 treatments plus an untreated check, with 20 replicates per treatment arranged in a randomized block design. Aqueous solutions of CPPA (1000 mg TOC/L) and NaCl (5000 mg/L "salt") were used for this experiment and all pots were treated with a soil drench application immediately after the seeds were planted. All seed was planted at the same depth (~5 mm below the soil surface) and the same volume of drench solution was applied to each pot regardless of the amount of CPPA or NaCl present in that volume. Treatments contained CPPA alone, salt alone, or CPPA plus salt. Two rates of CPPA were used; the first was equivalent to 520 mg of TOC per hectare and a second equivalent to 1040 mg of TOC per hectare. The salt rates were equivalent to 1.3 g and 2.6 g of NaCl per hectare. Treatments are summarized in Table 11.

TABLE 11

Summary of Experimental Treatments of Experiment Salt-3

| TRT. | Formulation | Rate (mg/ha) | Salt/TOC |
|---|---|---|---|
| 1 | UTC | | |
| 2 | CPPA (1000 mg/L TOC) | 520 | |
| 3 | CPPA (1000 mg/L TOC) | 1040 | |
| 4 | NaCl (5000 mg/L) | 1300 | |
| 5 | NaCl (5000 mg/L) | 2600 | |

TABLE 11-continued

Summary of Experimental Treatments of Experiment Salt-3

| TRT. | Formulation | Rate (mg/ha) | Salt/TOC |
|---|---|---|---|
| 6 | CPPA (1000 mg/L TOC) | 520 | 2.5 |
|   | NaCl (5000 mg/L) | 1300 | |
| 7 | CPPA (1000 mg/L TOC) | 520 | 5.0 |
|   | NaCl (5000 mg/L) | 2600 | |
| 8 | CPPA (1000 mg/L TOC) | 1040 | 1.25 |
|   | NaCl (5000 mg/L) | 1300 | |
| 9 | CPPA (1000 mg/L TOC) | 1040 | 2.5 |
|   | NaCl (5000 mg/L) | 2600 | |

Figure 19:
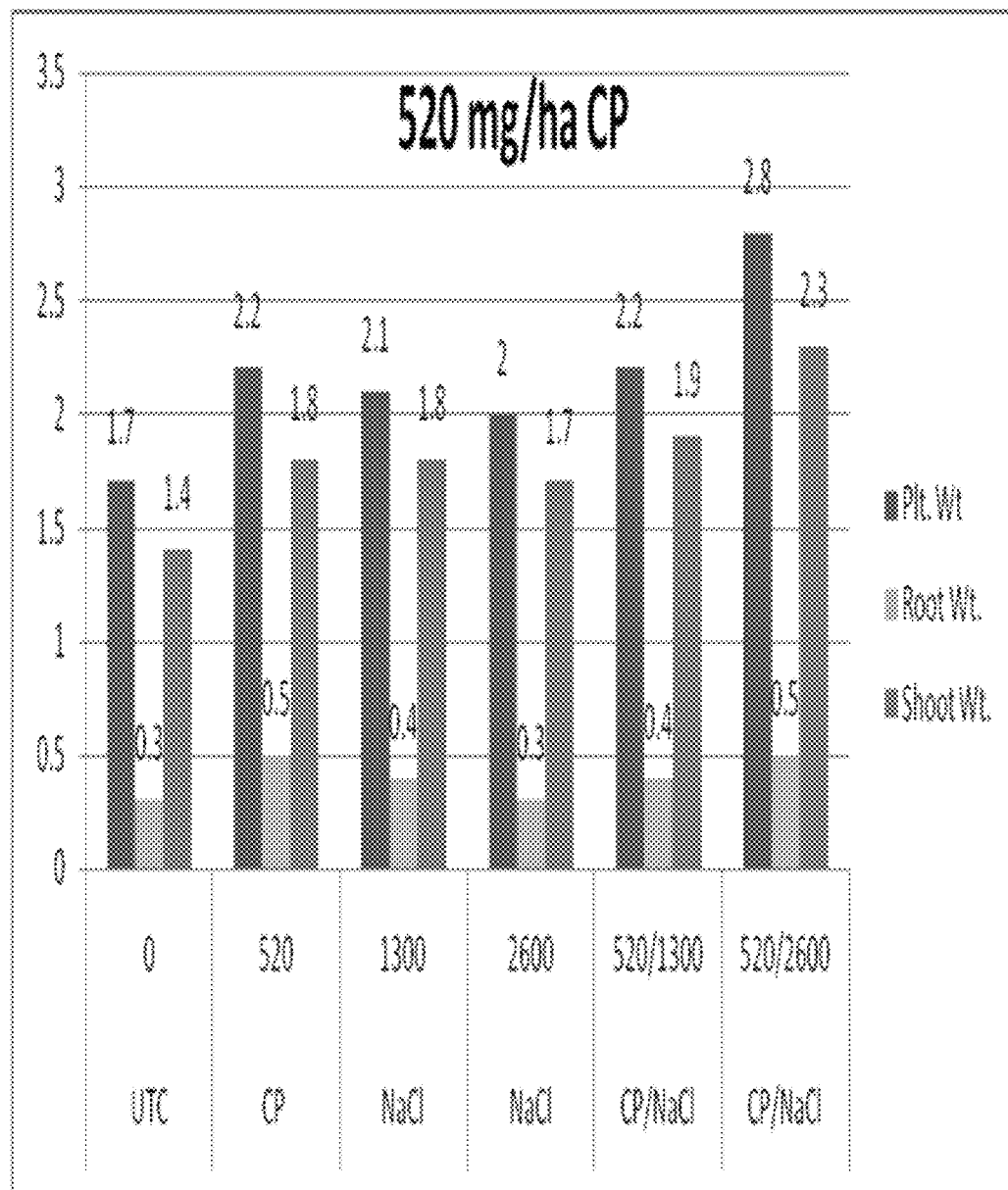
FIG. 19. Graphical representation of plant weight, plant root weight, and plant shoot weight verses control after treatment with embodiments of the present disclosure.

Twenty eight days after treatment the plants were assessed for plant weight, root weight, and shoot weight. FIG. 19 depicts plant weight, root weight, and shoot weight results for treatments with 520 mg CPPA/ha in combination with varying salt rates, which are summarized in Table 12.

TABLE 12

Summary of Biological Effects of Compositions applied at 520 mg/ha CPPA rate with 1300 mg/ha and 2600 mg/ha salt.

| Treatment | Formulation | Rate (mg/ha) | Plt. Wt | Root Wt. | Shoot Wt. |
|---|---|---|---|---|---|
| 1 | UTC | 0 | 1.7e | 0.3d | 1.4d |
| 2 | CP | 520 | 2.2bc | 0.5a | 1.8c |
| 3 | NaCl | 1300 | 2.1cd | 0.4bc | 1.8c |
| 4 | NaCl | 2600 | 2d | 0.3cd | 1.7c |
| 5 | CP/NaCl | 520/1300 | 2.2b | 0.4bc | 1.9b |
| 6 | CP/NaCl | 520/2600 | 2.8a | 0.5a | 2.3a |

Figure 20:
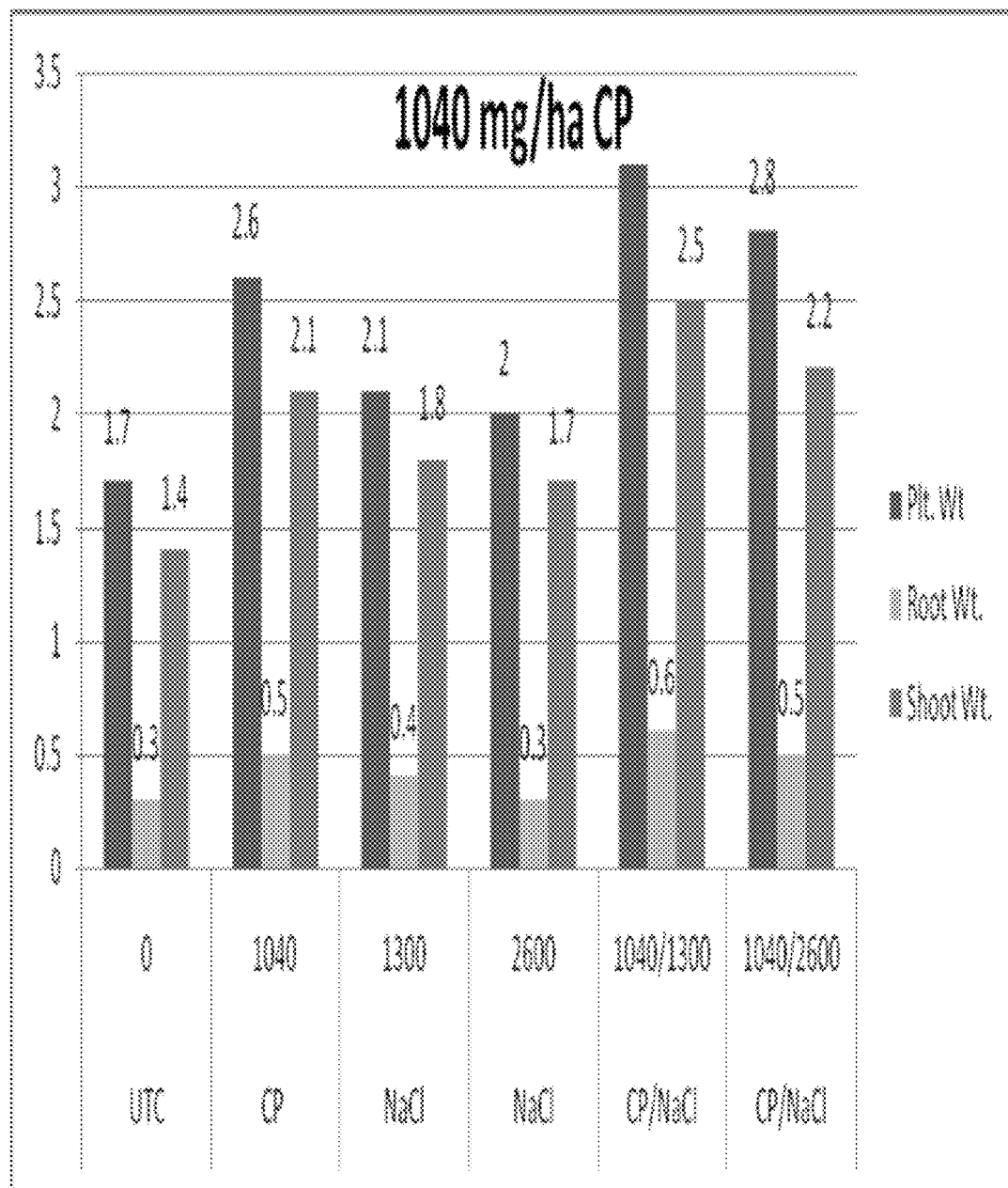
FIG. 20 Graphical representation of plant weight, plant root weight, and plant shoot weight verses control after treatment with embodiments of the present disclosure.

FIG. 20 depicts plant weight, root weight, and shoot weight results for treatments with 1040 mg CPPA/ha in combination with varying salt rates, which are summarized in Table 13.

TABLE 13

Results for treatments with 1040 mg CP/hectare

| Treatment | NaCl/TOC | Plt. Wt | Root Wt. | Shoot Wt. |
|---|---|---|---|---|
| UTC | | 1.7f | 0.3e | 1.4e |
| CP (1040 mg TOC/ha) | | 2.6c | 0.5b | 2.1c |
| NaCl (1300 mg NaCl/ha) | | 2.1de | 0.4cd | 1.8d |
| NaCl (2600 mg NaCl/ha) | | 2e | 0.3de | 1.7d |
| CP (1040 mg TOC/ha)/NaCl (1300 mg/ha) | 1.25 | 3.1a | 0.6a | 2.5a |
| CP (1040 mg TOC/ha)/NaCl (2600 mg/ha) | 2.5 | 2.8b | 0.5b | 2.2b |

In experiment Salt-3, the soil treatment of CPPA, at either 520 mg/ha or 1040 mg/ha rate, in combination with salt yielded superior results compared to the untreated check (UTC). The combination of CPPA and salt resulted in greater plant weights than for either the CPPA or salt alone. FIG. 19 shows a synergistic biological effect for soil treatment by the combination of CPPA and salt, the synergistic effect being greater for the 520 mg/ha rate of CPPA in combination with the higher salt rate (Treatment 6 of Table 12).

FIG. 20 shows that at high rates of CPPA application, e.g., 1040 mg/ha in combination with the lower rate of salt provided the greatest biological effect for plants, in this case, wheat. Likewise, the data of FIG. 20 shows a synergistic effect even for the low rate of salt in combination with CPPA, with an additive biological effect noted at the high salt rate.

The aforementioned experimental results show that CPPA in combination with cationic species can improve biological processes in plants when applied to the plant, or locus, and/or seed. In particular, experimental results show that CPPA in combination with transition metal cations such as iron, and/or alkali (earth) cations such as sodium, as aqueous soluble salts thereof, effect plant biology unexpectedly, providing improved leaves per plant, total plant weight, root/shoot weights, as well as leaf conductance. These attributes further provide for improved yields of such crops in agricultural or horticultural conditions.

All patents and publications cited herein are incorporated by reference into this application in their entirety. The words "comprise", "comprises", and "comprising" are to be interpreted inclusively rather than exclusively.

The invention claimed is:

1. A method of effecting at least one positive biological effect in a plant, the method comprising providing an aqueous mixture of:
   (i) an amount of concentrated, substantially metal-free complex polymeric polyhydroxy acids (CPPA) of between about 1000 ppm to about 500,000 ppm having a predetermined amount of total organic carbon (TOC) combined with:
      (a) a non-agriculturally effective amount of an agriculturally acceptable source of one or more transition metal ions; and
      (b) a phytotoxic amount of sodium chloride;
   wherein the positive biological effect is one or more of improved leaves per plant, total plant weight, root/shoot weights, leaf conductance, and yield;
   wherein the weight/weight ratio of metal salt to total organic carbon (TOC) in the mixture is at between about 0.1 to about 0.5; or weight/weight ratio of sodium chloride to TOC is between about 1.0 to about 10.0; and wherein the aqueous mixture is suitable for contacting a seed, or dilution for contact of a plant or its locus.

2. The method of claim 1, wherein the complex polymeric polyhydroxy acids are derived from partially humified organic material.

3. The method of claim 2, wherein the complex polymeric polyhydroxy acids comprise at least two of:
   a. a mixture of condensed hydrocarbons, lignins, and tannins and/or condensed tannins;
   b. a oxygen-to-carbon ratio is greater than about 0.5 for dissolved organic matter (DOM) present in the aqueous mixture;
   c. a total number of tannin compounds greater than about 200, the tannin compounds having a hydrogen to carbon ration of about 0.5 to about 1.4, and an aromaticity index of less than about 0.7 as measured by mass spectroscopy; or
   d. a mass distribution of about 55-60% lignin compounds, 27-35% tannin compounds, and about 8-15% condensed hydrocarbon as measured by mass spectroscopy.

4. The method of claim 3, wherein the complex polymeric polyhydroxy acids comprise a mixture of condensed hydrocarbons, lignins, and tannins and/or condensed tannins, characterized in that at least 10% of the total % of compounds of the composition are tannins and/or condensed tannins.

5. The method of claim 3, wherein the complex polymeric polyhydroxy acids comprise a mixture of condensed hydrocarbons, lignins, and tannins and/or condensed tannins, characterized in that at least 20% of the total % of compounds of the composition are tannins and/or condensed tannins.

6. The method of claim 1, wherein the transition metal ion is at least one of ferrous/ferric ions; manganese ions; copper ions; magnesium ions; molybdenum ions, and zinc ions.

7. The method of claim 1, further comprising contacting a part of a seed with the aqueous mixture at a loading of 0.1 mg/Kg seed to about 100 mg/Kg seed.

8. The method of claim 7, wherein the mixture is applied at a rate of about 0.001 gram/hectare to about 100 gram/hectare, with.

9. The method of claim 7, wherein the mixture is applied to a seed at a loading of 0.1 mg/Kg seed to about 100 mg/Kg seed and subsequently applied to the locus of the seed or a plant from the seed at a rate of about 0.001 gram/hectare to about 100 gram/hectare.

10. The method of claim 1, further comprising one or more pesticides.

11. A composition of matter comprising
   an aqueous concentrate mixture of (i) essentially metal-free complex polymeric polyhydroxy acids of between about 1000 ppm to about 500,000 ppm having a predetermined amount of total organic carbon (TOC); and
   (ii) one or more of (a) an added phytotoxic amount of sodium chloride; and (b) an added non-agriculturally effective amount of at least one source of an agriculturally acceptable transition metal ion,
   wherein the mixture is at least 0.1 to 0.5 weight/weight transition metal cation to the predetermined amount of TOC, or wherein the mixture is at least 1 to 10 weight/weight ratio of sodium chloride to TOC.

12. The composition of matter of claim 11, wherein the complex polymeric polyhydroxy acids are derived from partially humified organic matter.

13. The composition of matter of claim 11, wherein the complex polymeric polyhydroxy acids comprise two or more of:

a. a mixture of condensed hydrocarbons, lignins, and tannins and/or condensed tannins;
b. a oxygen-to-carbon ratio is greater than about 0.5 for dissolved organic matter (DOM) present in the aqueous mixture;
c. a total number of tannin compounds greater than about 200, the tannin compounds having a hydrogen to carbon ratio of about 0.5 to about 1.4, and an aromaticity index of less than about 0.7 as measured by mass spectroscopy; or
d. a mass distribution of about 55-60% lignin compounds, 27-35% tannin compounds, and about 8-15% condensed hydrocarbon as measured by mass spectroscopy.

14. The composition of claim 11, wherein the complex polymeric polyhydroxy acids comprise a mixture of condensed hydrocarbons, lignins, and tannins and/or condensed tannins, characterized in that at least 10% of the total % of compounds of the composition are tannins and/or condensed tannins.

15. The composition of claim 11, wherein the complex polymeric polyhydroxy acids comprise a mixture of condensed hydrocarbons, lignins, and tannins and/or condensed tannins, characterized in that at least 20% of the total % of compounds of the composition are tannins and/or condensed tannins.

16. The composition of claim 11, wherein the weight/weight ratio of the total amount of transition metal ion to total organic carbon (TOC) in the mixture is at between about 0.1 to about 0.5; or weight/weight ratio of sodium chloride to TOC is between about 1.0 to about 10.0, the total amount of transition metal ion comprising at least one of manganese, zinc, or copper ions, alone or in combination with iron ions.

17. A granular form comprising the mixture of claim 11.

18. The granular form of claim 17, further comprising at least one coating, the at least one coating at least partially surrounding the granular form, the first coating comprising the essentially metal-free complex polymeric polyhydroxy acids.

19. The granular form of claim 18, further comprising a second coating, the second coating at least partially surrounding the first coating, wherein the phytotoxic amount of sodium chloride and/or the synergistic amount of at least one source of an agriculturally acceptable transition metal ions is contained in the second coating.

20. The granular form of claim 19, wherein the first coating degrades at a first predetermined time and the second coating degrades at a second predetermined time.

21. A seed or seed coating comprising the mixture of claim 11 present at an amount of about 0.1 mg/Kg seed to about 100 mg/Kg seed.

22. A composition of matter comprising an aqueous concentrate mixture of (i) essentially metal-free complex polymeric polyhydroxy acids of between about 1000 ppm to about 500,000 ppm having a predetermined amount of total organic carbon (TOC); and a phytotoxic amount of one or more alkali metal or alkali earth metal salts normally present in salt water or brackish water, wherein the mixture is at least 1 to 10 weight/weight ratio of the alkali metal or the alkali earth metal salt to TOC.

* * * * *